United States Patent
Khan et al.

(10) Patent No.: US 12,318,412 B2
(45) Date of Patent: Jun. 3, 2025

(54) FAECALIBACTERIUM PRAUSNITZII AND DESULFOVIBRIO PIGER FOR USE IN THE TREATMENT OR PREVENTION OF DIABETES AND BOWEL DISEASES

(71) Applicant: METABOGEN AB, Gothenburg (SE)

(72) Inventors: Muhammad-Tanweer Khan, Mölndal (SE); Fredrik Backhed, Kullavik (SE)

(73) Assignee: BIOGAIA AB, Stockholm (SE)

( * ) Notice: Subject to any disclaimer, the term of this patent is extended or adjusted under 35 U.S.C. 154(b) by 359 days.

(21) Appl. No.: 17/577,208

(22) Filed: Jan. 17, 2022

(65) Prior Publication Data

US 2022/0133814 A1 May 5, 2022

Related U.S. Application Data

(63) Continuation of application No. 15/771,619, filed as application No. PCT/EP2016/076038 on Oct. 28, 2016, now Pat. No. 11,260,082.

(30) Foreign Application Priority Data

Oct. 28, 2015 (GB) ..................... 1519088

(51) Int. Cl.
  A61K 35/741 (2015.01)
  A61K 35/74 (2015.01)
  C12N 1/20 (2006.01)
  C12R 1/01 (2006.01)
(52) U.S. Cl.
  CPC ............ *A61K 35/741* (2013.01); *A61K 35/74* (2013.01); *C12N 1/20* (2013.01); *C12N 1/205* (2021.05); *C12R 2001/01* (2021.05)
(58) Field of Classification Search
  CPC .......... C12N 1/20; C12N 1/205; A61K 35/74; A61K 35/741; C12R 2001/01
  See application file for complete search history.

(56) References Cited

U.S. PATENT DOCUMENTS

2014/0199281 A1 7/2014 Henn et al.
2014/0234260 A1* 8/2014 Borody ................ A61K 9/4891 424/93.3
2015/0246081 A1 9/2015 Kenneth

FOREIGN PATENT DOCUMENTS

WO 2014137211 A1 9/2014
WO 2014152338 A1 9/2014

OTHER PUBLICATIONS

Duncan et al. "Growth requirements and fermentation products of *Fusobacterium prausnitzii*, and a proposal to reclassify it as *Aecalibacterium prausnitzii* gen. nov., comb. nov.", International Journal of Systematic and Evolutionary Microbiology (2002), 52, 2141-2146 DOI: 10.1099/ijs.0.02241-0 (Year: 2002).*
Foditsch et al. "Isolation and Characterization of Faecalibacterium prausnitzii from Calves and Piglets", PLOS One | DOI: 0.1371/journal.pone.0116465 Dec. 31, 2014 (Year: 2014).*
Loubinoux et al., "Reclassification of the only species of the genus *Desulfomonas, Desulfomonas pigra*, as *Desulfovibrio piger* comb. nov.", International J of Systematic and Evolutionary Microbiology, vol. 52, Issue 4, Jul. 2002 (Year: 2002).*
Cristina Maderuelo, Jose M. Lanao, Aránzazu Zarzuelo (2019) Enteric coating of oral solid dosage forms as a tool to improve drug bioavailability. European Journal of Pharmaceutical Sciences, vol. 138, 105019, ISSN 0928-0987, https://doi.org/10.1016/j.ejps.2019. 105019. (Year: 2019).*
Heinken et al., "Functional Metabolic Map of Faecalibacterium prausnitzii, a Beneficial Human Gut Microbe" Journal of Bacteriology, 196(18):3289-3302 2014.
Pham et al., "Lactate-utilizing community is associated with gut microbiota dysbiosis in colicky infants" Scientific Reports vol. 7, Article No. 11176 (2017).
"Written Opinion and International Search Report corresponding to International Application No. PCT/EP2016/076038, mailed Feb. 21, 2017, 12 pages".
Martín, Rebeca , et al., "The Commensal Bacterium Faecalibacterium prausnitzii Is Protective in DNBS-induced Chronic Moderate and Severe Colitis Models" Inflammatory Bowel Diseases, 20(3):417-430 (Mar. 2014).
Machiels, Kathleen , et al., "A decrease of the butyrate-producing species *Roseburia hominis* and Faecalibacterium prausnitzii defines dysbiosis in patients with ulcerative colitis", Gut DOI: 10.1136/gutjnl-2013-304833 (Sep. 2013) 12 pages.
Rey, Federico E, et al., "Metabolic niche of a prominent sulfate-reducing human gut bacterium", PNAS 110 (33):13582-13587 (Aug. 13, 2013).
Rios-Covian, David , et al., "Enhanced butyrate formation by cross-feeding between Faecalibacterium prausnitzii and Bifidobacterium adolescentis", FEMS Microbiology Letters 362(21):1-7 (Sep. 2015).
Sato, Tadashi , et al., "Isolation of lactate-utilizing butyrate-producing bacteria from human feces and in vivo administration of Anaerostipes caccae strain L2 and galacto-oligosaccharides in a rat model", FEMS Microbiol Ecol 66:528-536 (Jun. 12, 2008).
"Desulfovibrio piger DSM 749, Type strain", DSMZ-German Collection of Microorganisms and Cell Cultures GmbH. Retrieved from https://www.dsmz.de/collection/catalogue/details/culture/DSM-749 on Dec. 27, 2024 (5 pages).

* cited by examiner

*Primary Examiner* — Ruth A Davis
(74) *Attorney, Agent, or Firm* — Myers Bigel, P.A.

(57) ABSTRACT

The present invention relates generally to medicine. More specifically the invention relates to the use of synergistic probiotic bacteria as intervention for health.
In particular, the present invention provides a strain of *Faecalibacterium prausnitzii* and a bacterial strain which has one or more of the characteristics of: (i) being acetate producing, (ii) being lactate consuming and (iii) having the ability to be an electron acceptor, for use in the treatment or prevention of a disease associated with reduced butyrate levels or a disease associated with reduced or low numbers of *Faecalibacterium prausnitzii* bacteria.

18 Claims, 6 Drawing Sheets

FAECALIBACTERIUM PRAUSNITZII AND DESULFOVIBRIO PIGER FOR USE IN THE TREATMENT OR PREVENTION OF DIABETES AND BOWEL DISEASES

FIELD OF THE INVENTION

The present invention relates generally to medicine. More specifically the invention relates to the use of synergistic probiotic bacteria as intervention for health. The invention discloses a method that supports the growth and colonization in humans of a strain of the species *Faecalibacterium prausnitzii*.

BACKGROUND OF THE INVENTION

Within the body of a healthy adult, microbial cells are estimated to outnumber human cells by a factor of ten to one. These communities, however, remain largely unstudied, leaving almost entirely unknown their influence upon human development, physiology, immunity, nutrition and health.

Traditional microbiology has focused on the study of individual species as isolated units. However many, if not most, have never been successfully isolated as viable specimens for analysis, presumably because their growth is dependent upon a specific microenvironment that has not been reproduced experimentally. Among those species that have been isolated, analyses of genetic makeup, gene expression patterns, and metabolic physiologies have rarely extended to inter-species interactions or microbe-host interactions. Advances in DNA sequencing technologies have created a new field of research, called metagenomics, allowing comprehensive examination of microbial communities, even those comprised of uncultivable organisms. Instead of examining the genomes of individual bacterial strains that have been cultured in a laboratory, the metagenomic approach allows analysis of genetic material derived from complete microbial communities harvested from natural environments. For example, the gut microbiome complements our own genome with metabolic functions that affects human metabolism and may thus play an important role in health and disease.

It is believed the change of these bacteria in the intestines play a role in many chronic and degenerative diseases. There is a growing body of evidence that substantiates and clarifies what is called "the dysbiosis theory".

The term "dysbiosis" was originally coined by the Nobel laureate Eli Metchnikoff to describe altered pathogenic bacteria in the gut. Dysbiosis has by some been defined as "qualitative and quantitative changes in the intestinal flora, their metabolic activity and their local distribution." Thus dysbiosis is a state, often associated with reduced microbial diversity, in which the microbiota produces harmful effects via, for example:

qualitative and quantitative changes in the intestinal flora itself;
changes in their metabolic activities; and
changes in their local distribution.

The dysbiosis hypothesis states that the modern diet and lifestyle, and also the use of antibiotics and various antimicrobials in the environment, have led to the disruption of the normal intestinal microbiota. These factors result in alterations in bacterial metabolism, as well as the overgrowth of potentially pathogenic microorganisms. Altered microbiota is now believed to play a role in several disease conditions, including disorders like irritable bowel syndrome (IBS), inflammatory bowel disease (IBD), gout, pouchitis, chronic kidney disease, psoriasis, frailty and various metabolic diseases including obesity and type 2 diabetes.

Type 2 diabetes (T2D) is a metabolic disorder characterized by hyperglycemia and defects in insulin secretion and action. T2D is on the rise worldwide and an estimated 350 million people will be affected by 2030. This chronic disease is associated with multiple metabolic and cardiovascular comorbidities, and increased mortality from cardiovascular complications. Equally alarming is the fact that about half of all patients with T2D are newly detected, and many of them have cardiovascular complications at the time of diagnosis. Long before diabetes develops, impaired glucose tolerance (IGT) and other metabolic defects may appear. Since pharmacological and lifestyle interventions can reduce or postpone diabetes, especially in subjects with IGT, early detection of individuals at risk of T2D is important for prevention and for reducing the costs of medical care.

T2D is a result of complex gene-environment interactions, and several risk factors have been identified, including age, family history, diet, sedentary lifestyle, and obesity. The newly added factors associated to the microbiota composition, including the presence of specific bacterial genera and species in the gastro intestinal tract of a person can be used alone, or in combination with other measurements such as Body Mass Index (BMI), waist-to-hip ratio (WHR), waist circumference (WC) and specific markers, to better predict whether an individual is at risk for developing type 2 diabetes. Further can the information related to specific changes of the microbiota composition be used to formulate intervention options to correct the specific dysbiosis using certain probiotic products.

The gut microbiota has been proposed as an environmental factor that affects body metabolism and insulin sensitivity and has also been found to be altered in obesity. However, the relationship between the gut microbiota and T2D has not until recently been studied in large human cohorts, for example in the study by Karlsson et al. (Nature, Jun. 6, 2013). In addition, some gut microbial markers have recently been associated to T2D, for example in the metagenomic study of Chinese diabetic patients published by Qin et al. (Nature, Sep. 26, 2012).

During pregnancy—usually around the 24th week—many women develop gestational diabetes (GDM). History of previous gestational diabetes is known to be a risk condition for later development of type 2 diabetes. High glycemic levels during pregnancy or after delivery, are strong predictors of diabetes development in women. Relative hyperglycemia typically indicates some degree of insulin resistance and beta-cell dysfunction, which can be observed in such women, even with normal body weight and glucose tolerance.

Identifying and treating women with GDM is also important to minimize maternal and neonatal morbidity, preeclampsia and problems with high birth weights. Many of the immune and metabolic changes occurring during normal pregnancy are similar to those also described in the metabolic syndrome. The gut microbiota can, as described above, play a role in various diseases associated with the metabolic syndrome. A study by Koren et al. (Cell. 2012 Aug. 3) showed that the intestinal microbiota changes dramatically from first (T1) to third (T3) trimesters.

Inflammatory bowel disease (IBD) involves chronic inflammation of all or part of the digestive tract. IBD primarily includes ulcerative colitis and Crohn's disease. Both usually involve severe diarrhea, pain, fatigue and weight loss. Abundant data have incriminated intestinal bacteria in the initiation and amplification stages of IBD.

Gout is often characterized by recurrent outbreaks of inflammatory arthritis with a red, tender, hot, and swollen joint. This is associated with a lot of pain which typically comes on rapidly. The underlying mechanism involves elevated levels of uric acid in the blood and diagnosis may be confirmed by seeing the crystals in joint fluid or tophus. The cause of gout is a combination of diet and genetic factors. In recent decades, gout has become more common and the increases in onset and recurrences of gout likely reflect changes in demographic factors. Notable among these factors are increased longevity and age-associated cardiovascular, metabolic, and renal diseases in the population; the use of medications that alter urate balance as an unintended consequence of treatment for these chronic disorders; and increased dietary intake of foods and food additives that contribute to the development of obesity and diabetes mellitus.

Pouchitis is an inflammation of the lining of a pouch that is surgically created in the treatment of ulcerative colitis and certain other diseases. The pouch is attached internally to the area just above the anus to hold waste before it's eliminated. Pouchitis is the most frequently observed long-term complication of an ileal pouch-anal anastomosis (IPAA). Symptoms can include diarrhea, abdominal pain and joint pain, cramps, fever, increased number of bowel movements, nighttime fecal seepage, fecal incontinence, and a strong feeling of the need to have a bowel movement. The majority of patients with acute pouchitis respond to initial therapy with antibiotics, but approximately 60 percent have at least one recurrence.

Chronic kidney disease, sometimes also referred to as chronic kidney failure, is characterised by the gradual loss of kidney function and is further defined as the presence of kidney damage (usually detected as urinary albumin excretion of ≥30 mg/day, or equivalent) or decreased kidney function (defined as estimated glomerular filtration rate [eGFR]<60 mL/min/1.73 m2) for three or more months, irrespective of the cause. When chronic kidney disease reaches an advanced stage, dangerous levels of fluid, electrolytes and wastes can build up in the body. Available treatment for chronic kidney disease does focus on slowing the progression of the kidney damage. Chronic kidney disease can progress to end-stage kidney failure, which is fatal without artificial filtering (dialysis) or a kidney transplant.

Psoriasis is a common chronic skin disorder which is characterized by patches of abnormal skin. These patches can be red, itchy and scaly. Psoriasis is generally seen as a genetic disease which is triggered by environmental factors. No cure is available for the disease but there are various treatments that can help to control and balance the symptoms.

Frailty is a common geriatric syndrome that embodies an elevated risk of catastrophic declines in health and function among older adults. There is no gold standard for diagnosing frailty, however frail patients often present an increased burden of symptoms and medical complexity and reduced tolerance for medical interventions.

The connection between gut microbiota and energy homeostasis and inflammation and its role in the pathogenesis of obesity are increasingly recognized. Animal models as well as human data connect an altered microbiota composition to the development of obesity in the host through several mechanisms.

The bacterial species *Faecalibacterium prausnitzii* is one of the most abundant bacteria in the human gut ecosystem and it is an important supplier of various metabolites to the intestinal epithelium. Low or depleted numbers of *Faecalibacterium* have been associated with for example IBD, gout, pouchitis, chronic kidney disease, psoriasis, frailty and also T2D and GDM. Some have suggested the use of certain sources of substrates that promote growth of beneficial bacteria, such as for example carbon, so called prebiotics, including inulin, as a way to increase the biomass of for example *Faecalibacterium*. One potential problem with that approach is that firstly the specific strains of *Faecalibacterium* must be present in the gastro intestinal tract, secondly the prebiotic must reach the location where the targeted *Faecalibacterium* strains are located and thirdly, and importantly, the prebiotic may also "feed" other bacteria, which may be highly unwanted, especially when a targeted intervention is needed.

A preferred approach for intervention would be to give a probiotic product containing the wanted strains and preferably also in such way to promote their activity and increase their biomass in the proper location of the gastrointestinal tract. However bacteria such as *Faecalibacterium* are very difficult to colonize after delivery to the human intestine. Another hurdle when isolating and culturing representatives of gut microbiota for developing new potential probiotics is the complexity of gut environment in terms of distinct niches and habitats. Also, several gut microbes are cross fed from other microbes and may also require some growth factors from the host. The present invention is intended to solve this problem.

Definitions

All terms used in the present specification are intended to have the meaning usually given to them in the art. For the sake of clarity, some terms are also defined below.

Throughout the text, the term "Type 2 diabetes" (T2D) is used to refer to a metabolic disorder characterized by hyperglycemia, insulin resistance and relative impairment in insulin secretion.

The term "metagenomics" refers to the application of modern genomics techniques to the study of communities of microbial organisms directly in their natural environments, bypassing the need for isolation and lab cultivation of individual species.

"Probiotics" are live microorganisms that, when administered in adequate amounts, confer a health benefit to the host.

"Synergy" is the interaction of two or more agents (for example two or more different microorganisms), entities, factors or substances so that their combined effect, "the synergistic effect" is greater than the sum of their individual effects.

"Symbiosis" is a close, prolonged association between two or more different organisms of different species that may, but does not necessarily, benefit each member.

SUMMARY OF THE INVENTION

The invention herein relates to methods and products for probiotic interventions in mammals based on certain anaerobic bacteria.

A primary object of the invention is to support the growth and colonization in humans of a strain of the species *Faecalibacterium prausnitzii* by utilizing a unique electron cross talk and symbiosis between the bacterial species *Faecalibacterium prausnitzii* and *Desulfovibrio piger* (or alternative strain as defined elsewhere herein). The symbiosis can lead to the synergistic effect of more butyrate production than *F. prausnitzii* alone, as well as resulting in an increase in biomass or numbers of *Faecalibacterium prausnitzii* in the gastrointestinal tract. Thus, the present invention provides methods for the increasing the growth and colonization (e.g. in the gastrointestinal tract, preferably in humans) of *Faecalibacterium prausnitzii* bacteria.

Another primary object of the invention is to use the symbiotic strains for treatment and or prevention of diseases associated with reduced butyrate production or diseases associated with reduced or low levels of *Faecalibacterium prausnitzii*. Thus, in one embodiment the present invention provides a strain of *Faecalibacterium prausnitzii* (*F. prausnitzii*) and/or a strain of *Desulfovibrio piger* (*D. piger*) for use in therapy, e.g. as probiotics.

Another object of the invention is to use a strain of *D. piger* (or alternative strain as described herein) for the treatment and/or prevention of diseases associated with reduced butyrate production or diseases associated with reduced or low levels of *Faecalibacterium prausnitzii*. *D. piger* will boost endogenous *F. prausnitzii*.

Any appropriate strain of *Faecalibacterium prausnitzii* can be used in the present invention. *Faecalibacterium prausnitzii* is an anaerobic bacteria and in particular, appropriate strains of *Faecalibacterium prausnitzii* will have (i) the ability to produce butyrate. In addition, appropriate strains of *Faecalibacterium prausnitzii* will have one or more (e.g. 1 or 2), or preferably all, of the ability to (ii) consume acetate, (iii) produce extracellular electrons and (iv) to produce lactate. In some embodiments, strains with features (i), (ii) and (iv) are used. Strains with the ability to produce lactate (in particular high or significant levels of lactate) are particularly preferred. Typically these *Faecalibacterium prausnitzii* strains are glucose fermenting which results for example in the conversion of glucose to lactate and butyrate.

Even though any appropriate strain of *Faecalibacterium prausnitzii* can be used in the present invention the inventors have identified some unique functions when comparing different strains of *Faecalibacterium prausnitzii*. Strains with the presence of the enzyme L-lactate dehydrogenase (or strains containing an L-lactate dehydrogenase gene which in turn results in production or expression of the active enzyme) provides the bacteria with better properties to produce lactate and are preferred as this is more beneficial for the *D. Piger* strain in their synergistic relationship. Exemplary L-lactate dehydrogenase genes or enzymes are defined as EC 1.1.1.27 genes/enzymes.

A particularly preferred strain of *Faecalibacterium prausnitzii* for use in the present invention is denoted herein as *Faecalibacterium prausnitzii* strain FBT-22 and has been deposited under the Budapest Treaty at DSMZ (Leibniz Institute DSMZ—German Collection of Microorganisms and Cell Cultures, Inhoffenstr. 7B, D-38124 Braunschweig, Germany) on Oct. 20, 2015 and has been given the accession number DSM 32186. This particular strain has L-lactate dehydrogenase and shows higher lactate production compared to other strains of *Faecalibacterium prausnitzii*. More lactate during growth provides more substrate for *D. piger* and therefore supports their interaction.

This strain, e.g. the isolated strain, and its use in therapy, e.g. as a probiotic, e.g. for the treatment of diseases as described elsewhere herein, provides a yet further aspect of the invention.

Another preferred strain of *Faecalibacterium prausnitzii* for use in the present invention is the strain denoted as A2-165, which is available from the DSMZ (Leibniz Institute DSMZ—German Collection of Microorganisms and Cell Cultures, Inhoffenstr. 7B, D-38124 Braunschweig, Germany) and has the accession number DSM 17677.

Similarly, for the *Desulfovibrio piger* strain component, it is envisaged that any appropriate strain of *Desulfovibrio piger* may be used. *Desulfovibrio piger* is an anaerobic bacteria and in particular, an appropriate *Desulfovibrio piger* strain will have one or more (e.g. 1 or 2), or preferably all, of the characteristics of being (i) acetate producing, (ii) lactate consuming and (iii) having the ability to be an electron acceptor (e.g. to reduce more sulfate to sulfide). In some embodiments, strains with features (i) and (ii) are used. Such strains can generally convert lactate to acetate. As these particular characteristics of *Desulfovibrio piger* bacteria are important for the symbiosis with the *Faecalibacterium prausnitzii* bacteria, it is envisaged that any other species of bacteria (i.e. alternative strains) which have these characteristics can also be used in the present invention. A particularly preferred strain of *Desulfovibrio piger* for use in the present invention is denoted herein as *Desulfovibrio piger* strain FBT-23 and has been deposited under the Budapest Treaty at DSMZ (Leibniz Institute DSMZ—German Collection of Microorganisms and Cell Cultures, Inhoffenstr. 7B, D-38124 Braunschweig, Germany) on Oct. 20, 2015 and has been given the accession number DSM 32187.

This strain, e.g. the isolated strain, and its use in therapy, e.g. as a probiotic, e.g. for the treatment of diseases as described elsewhere herein, provides a yet further aspect of the invention.

Preferably the *Faecalibacterium prausnitzii* and *Desulfovibrio piger* (or alternative) strains are used together as a combination therapy.

Preferably the strains for use in the invention are isolated strains, e.g. strains which are isolated from the human or animal body. Such strains are thus separate from other strains of microorganisms or other impurities from the human or animal body from which they are isolated, e.g. are pure cultures, except when two or more isolated strains are mixed or combined together for use in the present invention.

When the two strains interact (e.g. the *Faecalibacterium prausnitzii* and *Desulfovibrio piger* strains described above), for example are co-cultivated (co-cultured) or administered together, or otherwise come into contact with each other, then butyrate production is increased when both strains are present compared to the butyrate production by the *Faecalibacterium prausnitzii* strain alone. Preferably the effect on the increase in butyrate production is a synergistic effect. Where necessary, conditions or the environment in which the interaction or contact between the two strains used in the invention takes place can be selected to support butyrate production.

Thus, a yet further embodiment of the invention provides a composition or product comprising the *Faecalibacterium prausnitzii* and *Desulfovibrio piger* (or alternative) strains as defined herein either individually or in combination. Preferred combinations of bacteria are those that give rise to a synergistic effect on butyrate production when the strains interact with each other. Such interaction is a form of symbiosis.

As outlined above, the strains and combinations thereof as described herein have therapeutic utility, and can be used in the treatment or prevention of any disease which will benefit from increased production of butyrate or any disease which will benefit from an increase in number or colonization of *Faecalibacterium prausnitzii* bacteria. Appropriate diseases thus include any disease associated with reduced butyrate levels, e.g. reduced production of butyrate (or a depletion of butyrate or a lack of butyrate) caused for example by a reduction or depletion in microorganisms which produce butyrate, for example a disease associated with reduced or low number or depleted amounts of *Faecalibacterium prausnitzii* bacteria, or caused for example by a reduction in butyrate production by microorganisms which produce butyrate. Alternatively, the strains and combinations thereof as described herein can be used in the treatment or prevention of any disease associated with a reduction or depletion in microorganisms which produce butyrate, for example a disease associated with reduced or low number or depleted amounts of *Faecalibacterium prausnitzii* bacteria. These diseases are typically diseases of the gastrointestinal (GI) tract.

The reference to reduced levels, reduced production, or depletion or low levels, or low numbers, etc., will be readily understood and determined by a skilled person, for example by comparison to the levels found in an appropriate control, e.g. in a healthy patient. Thus, such levels or numbers etc., may be regarded as below normal, or sub-normal or abnormal, or otherwise less abundant than normal. Preferably such reductions (and indeed other reductions or decreases or negative effects as mentioned elsewhere herein) are measurable reductions, more preferably they are significant reductions, preferably clinically significant or statistically significant reductions, for example with a probability value of 50.05, when compared to an appropriate control level or value.

Indeed, where significant changes are described herein, it is preferred that such changes are statistically significant changes, for example with a probability value of ≤0.05, when compared to an appropriate control level or value.

Exemplary diseases are described elsewhere herein and include T2D, GDM, obesity, gout, pouchitis, chronic kidney disease, psoriasis, frailty, IBD, IBS, abdominal pain associated with IBS and constipation (or diseases associated with constipation). Preferred diseases to be treated are T2D or GDM. Another preferred disease or condition to be treated is dysbiosis.

Thus, viewed alternatively, the present invention provides therapeutic methods for the treatment or prevention of T2D, GDM, obesity, gout, pouchitis, chronic kidney disease, psoriasis, frailty, IBD, IBS, abdominal pain associated with IBS or constipation (or diseases associated with constipation) or other diseases or conditions as described herein (e.g. dysbiosis), or for the treatment or prevention of metabolic diseases, comprising the administration of probiotic strains as described herein.

In all embodiments described herein the term "disease associated with" can also refer to "disease characterised by".

The symbiotic and preferably synergistic effects of the two strains on each other result in the increased production of butyrate and in the increased growth and colonization of *Faecalibacterium prausnitzii* bacteria in the GI tract thereby alleviating and treating disease. Preferably, the strains are selected such that the total butyrate production by both strains when present together (e.g. in a co-culture or when administered together) is greater than the butyrate production observed with the *Faecalibacterium prausnitzii* bacteria alone and is preferably synergistic, i.e. the total butyrate production by both strains is greater (increased), preferably significantly greater (increased), than the sum of the individual levels of butyrate production.

The present invention thus further provides a strain of *Faecalibacterium prausnitzii* as described herein and a strain of *Desulfovibrio piger* (or alternative strain) as described herein for use in therapy by combined, sequential or separate administration.

Further provided is a product or composition comprising a strain of *Faecalibacterium prausnitzii* and a strain of *Desulfovibrio piger* (or alternative strain) as described herein as a combined preparation for separate, simultaneous or sequential use in the treatment or prevention of diseases as defined elsewhere herein.

Thus, the present invention provides a strain of *Faecalibacterium prausnitzii* (*F. prausnitzii*) and a strain of *Desulfovibrio piger* (*D. piger*) (or alternative strain) as described herein for use in the treatment of diseases as described herein, e.g. a disease associated with reduced levels or production of butyrate in the GI tract (for example due to a reduction or depletion in microorganisms which produce butyrate, for example a disease associated with reduced or low number or depleted amounts of *Faecalibacterium prausnitzii* bacteria, or a reduction in butyrate production by microorganisms which produce butyrate), or other diseases as described elsewhere herein.

Viewed alternatively, the present invention provides a strain of *Faecalibacterium prausnitzii* (*F. prausnitzii*) and a strain of *Desulfovibrio piger* (*D. piger*) (or alternative strain) as described herein for use in the manufacture of a medicament or composition for the treatment of diseases as described herein, e.g. a disease associated with reduced levels or production of butyrate in the GI tract (for example due to a reduction or depletion in microorganisms which produce butyrate, for example a disease associated with reduced or low number or depleted amounts of *Faecalibacterium prausnitzii* bacteria, or a reduction in butyrate production by microorganisms which produce butyrate), or other diseases as described elsewhere herein.

In an alternative aspect, the present invention provides the use of the products, strains or compositions as described herein in the manufacture of a medicament or composition for use in the treatment or prevention of diseases as described herein.

Viewed alternatively, the present invention provides a method of treating a disease as described herein, e.g. a disease associated with reduced levels or production of butyrate in the GI tract (for example due to a reduction or depletion in microorganisms which produce butyrate, for example a disease associated with reduced or low number or depleted amounts of *Faecalibacterium prausnitzii* bacteria, or a reduction in butyrate production by microorganisms which produce butyrate), or other diseases as described elsewhere herein, in a patient, said method comprising administration of an effective amount of a strain of *Faecalibacterium prausnitzii* (*F. prausnitzii*) and a strain of *Desulfovibrio piger* (*D. piger*) (or alternative strain) as described herein to said patient.

The administration of the probiotic strains in said methods of treatment and uses of the invention (or in any other methods of treatment or therapeutic uses as described herein) is carried out in pharmaceutically or physiologically effective amounts, to subjects in need of treatment. Thus, said methods and uses may involve the additional step of identifying a subject in need of treatment.

In all the embodiments described herein, preferred diseases to be treated are T2D or GDM. Preferred strains for use in therapy or in the treatment of the diseases described herein, and in particular T2D or GDM, are the *Faecalibacterium prausnitzii* strain DSM 32186 or the *Desulfovibrio piger* strain DSM 32187, which can also be used in combination. Another preferred *Faecalibacterium prausnitzii* strain is A2-165 (DSM 17677).

As set out above, a yet further aspect of the invention provides a strain of *D. piger* (or alternative strain as described herein) for use in the treatment or prevention of a disease associated with reduced butyrate levels or a disease associated with reduced or low numbers of *Faecalibacterium prausnitzii* bacteria.

Thus, the present invention also provides a strain of *D. piger* (or alternative strain as described herein) for use in the manufacture of a medicament or composition for the treatment of diseases as described herein.

The present invention also provides a method of treating a disease as described herein, in a patient, said method comprising administration of an effective amount of a strain of *Desulfovibrio piger* (or alternative strain as described herein) to said patient.

Preferred embodiments for said methods and uses, e.g. preferred strains of *Desulfovibrio piger* (or alternative strains) and preferred diseases are as described elsewhere herein. In such embodiments the administration of *D. piger* will boost or increase (e.g. increase the biomass or numbers of, or otherwise increase the growth or colonization of, as described elsewhere herein) the endogenous *F. prausnitzii* in the patient or subject, e.g. in the gastrointestinal tract of the patient or subject.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

Figure 1:
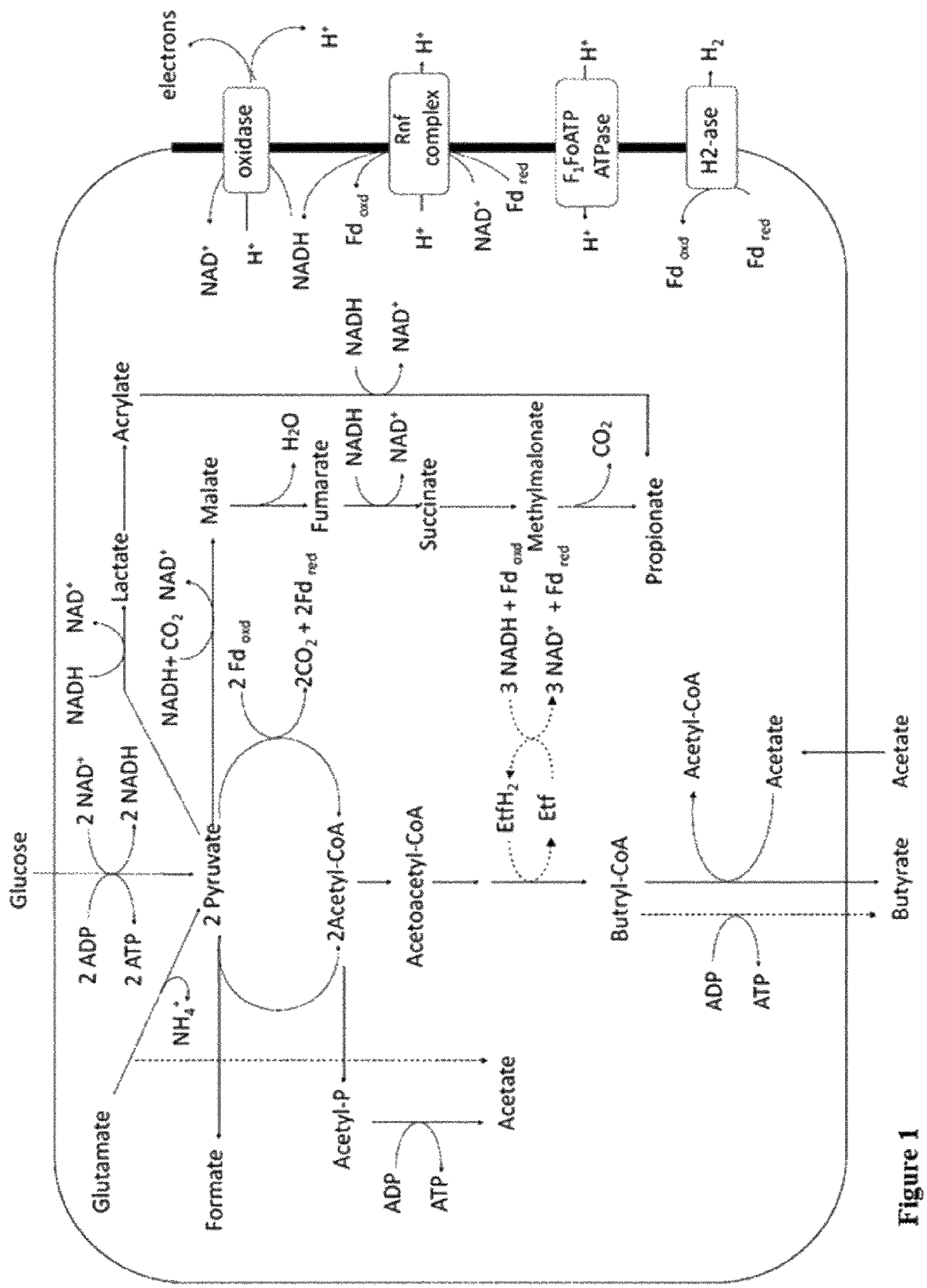
FIG. 1 shows the major fermentative pathway employed by gut microbiota in human gut.

As set out above, the invention herein relates to methods and products for probiotic interventions in mammals based on certain anaerobic bacteria.

It can be seen that in preferred embodiments of the invention, a combination or mixture of probiotic bacteria are administered (combination therapy). Such mixtures or combinations of probiotic bacteria can be administered together in a single (the same) composition or administered separately (e.g. in different products or compositions). If administered separately then such administration may be sequential or simultaneous. However, the separate administration forms part of the same therapeutic regimen or method.

In embodiments where the administration of the two strains is separate or sequential, it is preferred that the administrations are made within a reasonable time frame of each other. For example, the separate administrations are preferably made within hours (e.g. one hour) or minutes (e.g. within 15 or 30 minutes) of each other, most preferably within as short a timeframe as possible (including simultaneous or effectively simultaneous administration). Preferably the two strains of probiotic bacteria are co-administered in a single composition.

In embodiments where more than one strain of probiotic bacteria is used in a mixture in a single composition, or where more than one strain of probiotic bacteria is used but they are administered separately, then any appropriate ratio of the bacteria can be used providing that the probiotic function of the strains (for example increased butyrate production and preferably a synergistic effect on butyrate production) is retained to a useful extent. Such ratios can readily be determined by a person skilled in the art. For example, such a combination of two strains (e.g. *F. prausnitzii*: *D. piger* (or alternative strain)) might be used at a ratio of 1:10, 1:5, 1:1, 5:1, or 10:1 or anywhere between these extremes, e.g. 1:1. Such ratios may also be used in the products, kits, compositions, etc., of the invention as described elsewhere herein.

The present invention thus provides combination therapies using at least two strains of probiotic bacteria, preferably in which the strains have a symbiotic and more preferably a synergistic effect on each other, in particular in terms of increased butyrate production.

Such synergistic effects (or indeed increased effects) can readily be measured in vitro in order to select appropriate combinations of bacteria, for example by measuring the levels of butyrate production from each individual strain alone by any appropriate assay and then assessing whether the butyrate production of the strains in combination (e.g. when co-cultured or otherwise able to interact with each other) is greater, and preferably significantly greater, than the sum of the level of butyrate production by the individual strains. A simple increase (preferably a significant increase) in butyrate production can also be measured in this way. Appropriate assays may be carried out under anaerobic conditions. Appropriate exemplary methods are described in the Examples.

In the therapeutic methods and uses as described herein, the strains are administered in appropriate doses, formulations etc. such that butyrate production is increased in the GI tract of the mammal. In addition, preferably the numbers of *Faecalibacterium prausnitzii* bacteria are increased (e.g. the biomass of *Faecalibacterium prausnitzii* is increased) or growth and colonization of the *Faecalibacterium prausnitzii* bacteria within the GI tract is improved.

Preferably such increases (and indeed other increases, improvements or positive effects as mentioned elsewhere herein) are measurable increases, etc., (as appropriate), more preferably they are significant increases, preferably clinically significant or statistically significant increases, for example with a probability value of ≤0.05, when compared to an appropriate control level or value (e.g. compared to an untreated or placebo treated subject or compared to a healthy or normal subject, or the same subject before treatment).

The methods and uses of the present invention are suitable for the prevention of diseases as well as the treatment of diseases. Thus, prophylactic treatment is also encompassed by the invention. For this reason in the methods and uses of the present invention, treatment also includes prophylaxis or prevention where appropriate.

The methods and uses of the invention can be carried out on any mammal (patient or subject), for example humans or any livestock, domestic or laboratory animal. Specific examples include mice, rats, pigs, cats, dogs, sheep, rabbits, cows and monkey. Preferably, however, the mammal is a human.

In a further aspect of the invention kits or pharmaceutical packs are provided. Thus, the present invention provides a kit or pharmaceutical pack comprising (or consisting of):
(i) a strain of *Faecalibacterium prausnitzii* as defined herein, and
(ii) a strain of *Desulfovibrio piger* (or alternative strain) as defined herein; or a kit or pharmaceutical pack comprising (or consisting of):
a strain of *Desulfovibrio piger* (or alternative strain) as defined herein, for example to boost growth of endogenous *F. prausnitzii* as described elsewhere herein.

As described elsewhere herein, the two strains forming separate components of the kit can be administered as separate components or can be combined together before administration. In alternative embodiments of the kit, the two strains could be provided together as a single kit or pack component. Preferably such kits or packs are for use in the methods and uses of the present invention, for example for use in the treatment of diseases as defined herein. The kit or pack optionally also comprises instructions for administration of the components, or instructions for use of the kit or pack.

Earlier studies are indicating that the bacterial alterations observed in Type 2 diabetes (T2D) do not affect the overall composition of the microbiota but the abundance of a limited number of species. Specifically there is a reduction of bacteria producing the short chain fatty acid butyrate and that depletion of butyrate producing bacteria also reduces the levels of secondary bile acids. This seems to be true also in gestational diabetes (GDM) disease and other metabolic associated diseases. *Faecalibacterium*, which is a butyrate-producer with anti-inflammatory effects, also depleted in inflammatory bowel disease, has been reported to be less abundant on average in pregnant women with GDM at the third trimester (T3).

Based on our own studies in healthy humans and humans with disease using metagenome analysis we isolated several strains of *Faecalibacterium prausnitzii* from human faeces and selected the most promising ones for further development as potential probiotic strains. Based on these studies, appropriate strains of *Faecalibacterium prausnitzii* for use in the present invention are described elsewhere herein. A preferred strain is FBT-22 (DSM 32186). This particular strain has the L-lactate dehydrogenase gene and shows higher lactate production compared to other strains of *Faecalibacterium prausnitzii*. Indeed, as mentioned elsewhere herein, strains with the ability to produce lactate (in particular high or significant levels of lactate) are particularly preferred. Exemplary appropriate levels of lactate production by the strains for use in the invention are those which are sufficient to have a biological effect, for example a positive effect on the growth of *D. piger* upon co-culture. Exemplary levels are levels of at least 10 mM, 20 mM, 30 mM, 40 mM, 50 mM, or 60 mM, e.g. when strains are cultured in an appropriate growth medium, e.g. PGM or LYBHI as described in the Examples. Exemplary high levels of lactate production are levels of at least 35 mM, 40 mM, 45 mM, 50 mM, 55 mM or 60 mM, e.g. when strains are cultured in an appropriate growth medium, e.g. PGM or LYBHI as described in the Examples. Strains which contain a L-lactate dehydrogenase gene (or express an active L-lactate dehydrogenase enzyme) are particularly preferred.

As mentioned elsewhere herein, *Faecalibacterium prausnitzii* strains with the ability to produce butyrate are particularly preferred. Exemplary appropriate levels of butyrate production by the strains for use in the invention are those which are sufficient to have a biological effect, for example a positive effect on T2D or other diseases as described herein. Exemplary levels are levels of at least 3 mM, 5 mM, 7 mM, 10 mM, or 15 mM, or up to 10 mM or 15 mM, e.g. when strains are cultured in an appropriate growth medium, e.g. PGM or LYBHI as described in the Examples. Preferably, in accordance with the present invention, the level of butyrate production is increased, preferably significantly increased, when the strain of *Faecalibacterium prausnitzii* is present in combination with a strain of *D. piger* (or alternative strains) compared to the butyrate production by *Faecalibacterium prausnitzii* alone. Preferably a synergistic increase is observed. Exemplary levels of increase are at least 1.5 fold, 2.0 fold, 2.5 fold, 3.0 fold or 3.5 fold.

*F. prausnitzii* is the most abundant bacterium in the human intestinal microbiota of healthy adults, representing up to more than 5% of the total bacterial population. Over the past five years, an increasing number of studies have clearly described the importance of this highly metabolically active commensal bacterium as a component of the healthy human microbiota. Changes in the abundance of *F. prausnitzii* have been linked to dysbiosis in several human disorders.

*F. prausnitzii* is an extremely oxygen sensitive (EOS) bacterium and is difficult to cultivate even in anaerobic conditions. The major end products of glucose fermentation by *F. prausnitzii* strains are formate, lactate and substantial quantities of butyrate (>10 mM butyrate in vitro).

Some observations provide key insight in host-microbe interactions at the gut barrier of *F. prausnitzii*. The strain is:
Butyrate producing
Glucose fermenting
Acetate consuming
Able to produce extracellular electrons, e.g. capable to respire electrons to extracellular electron acceptors via riboflavin.
Using glucose as electron donor and flavin as mediator.

Considering the abundance and growth of *F. prausnitzii* in a healthy gut our assumption was that there must be other bacteria in the vicinity that can act in a symbiotic fashion and support the growth of *F. prausnitzii*. So by the identified characteristics we looked for a bacteria that is lactate consuming, acetate producing and also capable of acting as an electron acceptor. Based on these characteristics a strain can be chosen that together with *F. prausnitzii* act in a symbiotic fashion. One possible candidate was found in *Desulfovibrio piger* (and a particularly preferred strain of *Desulfovibrio piger* is FBT-23 (DSM 32187). However, any other strains with these properties (i.e. alternative strains) could also be used.

*Desulfovibrio* is one of the first genera described and probably the most thoroughly studied genus among the sulfate-reducing bacteria. They are sulfate-reducing, nonfermenting, anaerobic, gram-negative bacilli characterized by the presence of a pigment, desulfoviridin, which fluoresces red in alkaline pH and blue-green in acid pH under long-wavelength UV light. *D. piger* strains have never been isolated from outside the human body and can be considered natural inhabitants of the intestinal tract, where sulfates abound.

Some characteristics of the strain are the following:
Converts lactate or consumes lactate, a reduced fermentative metabolite of microbes, into the less reduced product acetate.

The conversion of lactate to acetate releases electrons, which reduces sulfate to sulfide.

*Desulfovibrio* cytochromes may act as electron acceptors from the surrounding reduced environment or bacteria and are utilized to reduce sulfate to sulfide.

To our surprise when a *F. prausnitzii* bacterial cell is in the vicinity of a *D. piger* bacterial cell there is a unique electron cross talk and symbiosis between *F. prausnitzii* and *D. piger*. This new discovery is utilised by the invention herein by making products based on the combination of selected strains of the two species to support the growth and colonization in humans of a strain of *F. prausnitzii*. Another possible product would be to use *D. piger* alone to administer, e.g. to humans, to support growth of endogenous *F. prausnitzii*.

Figure 2:
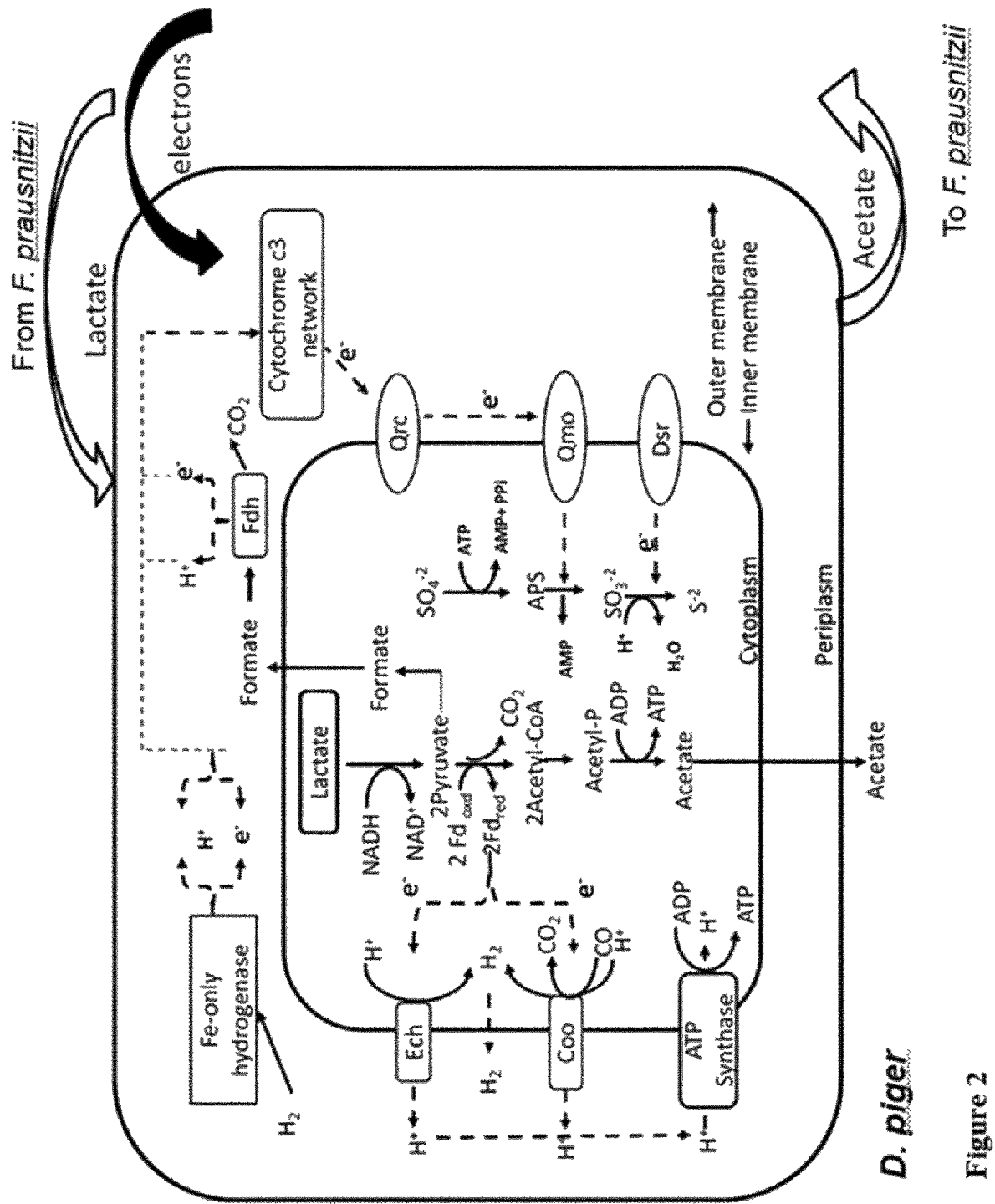
FIG. 2 shows the symbiosis between *F. prausnitzii* and *Desulfovibrio piger*.
Figure 2:
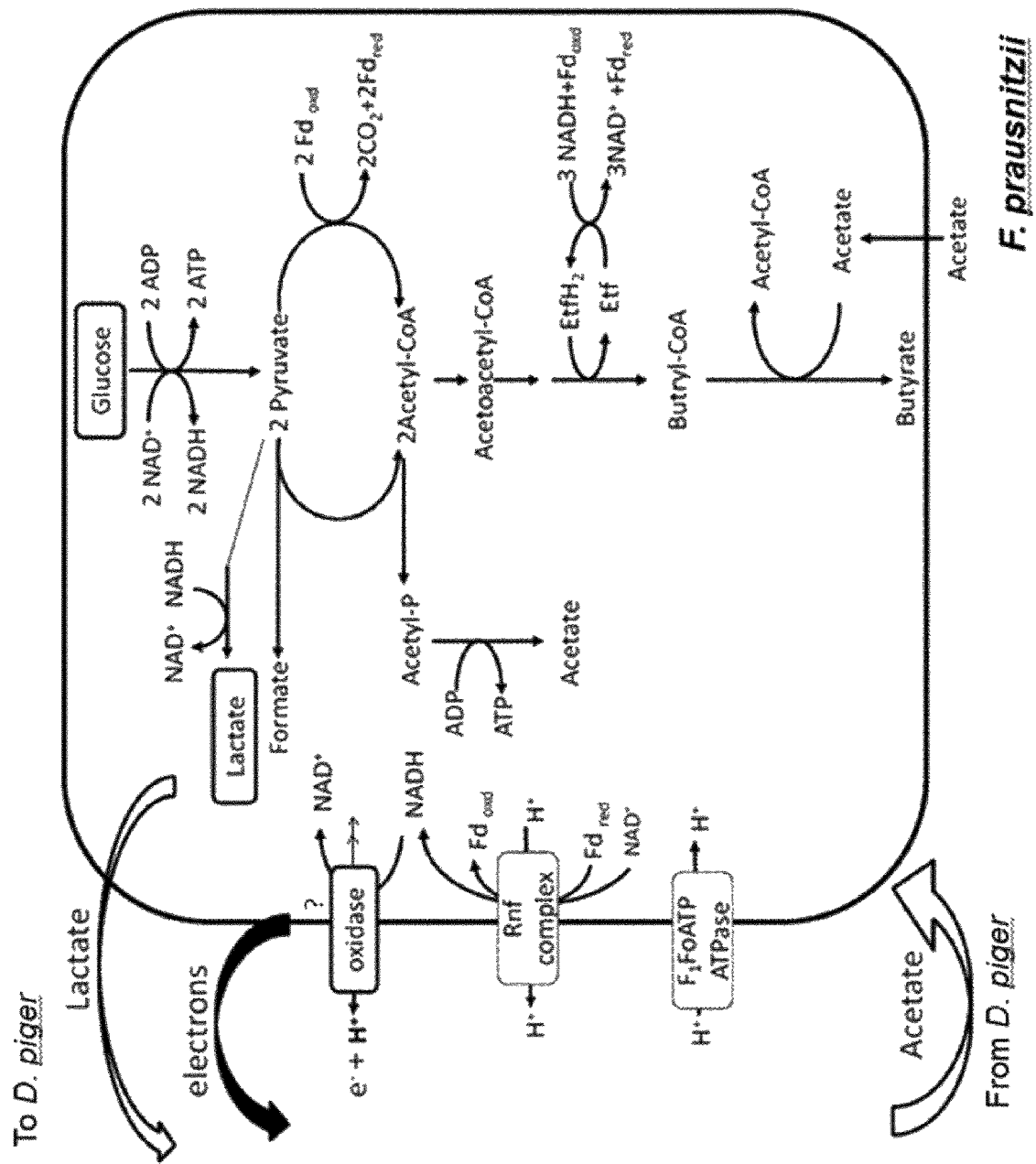

The symbiosis between the two species can in part be described by the following, see FIG. 2:

*F. prausnitzii* converts glucose to lactate and butyrate, consume acetate and produces extracellular electrons

*D. piger* converts lactate to acetate and accepts electrons to reduce more sulfate to sulfide.

Net results are better growth of both organisms and more butyrate production, showing a synergistic effect.

This interaction has been confirmed by showing higher butyrate accumulations in cocultures of *F. prausnitzii* and *D. piger* (see Example 4).

The symbiosis results in the wanted growth and multiplied production of butyrate by *F. prausnitzii* (see Example 4) to be used, according to the invention herein, for probiotic intervention in people at risk, or having, dysbiosis in their intestinal microbiota (e.g. gastrointestinal microbiota dysbiosis) where butyrate producing bacteria are reduced such as in T2D or GDM.

Appropriate probiotic strains for use in the invention can be obtained or isolated from any mammal which is capable of suffering from or is susceptible to gastrointestinal microbiota dysbiosis especially in T2D, GDM obesity, gout, pouchitis, chronic kidney disease, psoriasis, frailty, IBD, IBS, abdominal pain associated with IBS and constipation diseases, or other diseases as described herein. Humans are a preferred source. Appropriate sample types from which to obtain appropriate probiotic bacteria would be well known to a person skilled in the art. However fecal samples are preferred. Appropriate culture conditions are anaerobic conditions. Appropriate culture medium can be selected by a person skilled in the art, for example PGM medium or LYBHI or other medium as described in the Examples.

It is a further object of the invention to provide methods, kits, systems, compositions and products for said symbiosis.

Thus, the strains (or combinations thereof) as described herein may take the form of a compound (agent) or composition, e.g. a pharmaceutical compound or composition or a nutritional compound or composition.

The present invention thus also provides a composition or formulation comprising a *F. prausnitzii* strain as described herein and a *D. piger* strain or an alternative bacterial strain as described herein, e.g. which has one or more of the characteristics of: (i) being acetate producing, (ii) being lactate consuming and (iii) having the ability to be an electron acceptor; and at least one additional component selected from the group consisting of a carrier, diluent or excipient (for example a pharmaceutically acceptable carrier, diluent or excipient), a foodstuff or food supplement, or a further therapeutic or nutritional agent. Thus, said compositions can be formulated as pharmaceutical compositions or as nutritional compositions, e.g. as a food product.

Therapeutic uses of the strains, compositions and formulations of the invention as defined herein, are also provided.

An appropriate mode of administration and formulation of the strains, compositions, formulations, etc., is chosen depending on the site of disease. A preferred mode of administration is oral or rectal, however, equally intravenous or intramuscular injection may be appropriate.

Appropriate doses of the strains, compositions and formulations of the invention as defined herein can readily be chosen or determined by a skilled person depending on the disorder to be treated, the mode of administration and the formulation concerned. For example, a dosage and administration regime is chosen such that the probiotic bacteria (or combination of bacteria) administered to the subject in accordance with the present invention can result in a therapeutic or health benefit (e.g. an increase in the butyrate levels in the gastrointestinal tract or an increase in the growth of *F. prausnitzii* bacteria in the gastrointestinal tract or the treatment of disease). Thus, in embodiments of the invention where two different strains of bacteria are administered, an appropriate dose of each bacteria is selected such that a therapeutic or health benefit is observed when both strains are present. For example, daily doses of one or each bacteria of $10^1$ to $10^{12}$, for example $10^5$ to $10^{10}$, or $10^6$ to $10^8$, or $10^8$ to $10^{10}$ total CFUs of bacteria may be used. A preferred daily dose of one or each bacteria is around $10^8$ or $10^9$ total CFUs, e.g. $10^7$ to $10^{10}$ or $10^8$ to $10^{10}$ or $10^8$ to $10^9$.

Thus, products or compositions or formulations or kits containing strains as defined herein are provided. Preferred products or compositions comprise frozen, freeze-dried, lyophilized, or dried bacteria and are preferably in a unit-dosage format, e.g. a capsule or tablet or gel. Preferred products or compositions will contain both a *F. prausnitzii* strain and a *D. piger* (or alternative) strain. Appropriate ratios and doses (e.g. in the form of numbers of bacteria or CFUs) for use in such products, etc., are described elsewhere herein and in the Examples. Other components may also be included in such products, etc., for example preservatives (e.g. glycerol), stabilizers, gelling agents and/or cryoprotectants. In some embodiments such additional components are non-natural agents.

As shown in FIG. 1, theoretically homoacetate, homoformate and lactate production are the most energy efficient pathways in terms of electron disposal when glucose was used as electron donor. Homobutyrogenesis produces 4 moles of excess electrons per mole of glucose while lactate to acetate conversion yields 4 moles of electrons per mole of acetate production. Production of proprionate from glucose yields excess of 10 moles of electrons. During fermentation, this electron disproportion is balanced by mixed acid fermentation and gas productions. Some microbes respire electrons to extracellular electron acceptors such as nitrate, sulfate or insoluble metallic complex. Moreover, oxygen can acts as indirect electron acceptor as some of the gut microbes can consume oxygen in small amounts. The net result of microbial activities generates electron rich reducing environment in the human or animal gut, which keeps the net redox potential negative. This oxygen deficient reducing environment favours the growth of strict anaerobes in the gut lumen. Despite the fact that there is continuous influx of oxygen via ingestion of food and diffusion from gut mucosa the net redox potential of the gut remains negative, ca −300 mV.

The therapeutic uses of the invention as defined herein include the reduction, prevention or alleviation of the relevant disorder or symptoms of disorder (e.g. can result in the modulation of disease symptoms). Such relevant disorders are described elsewhere herein, for example those associated with lack of or depleted butyrate production or those associated with reduced or low numbers of F. prausnitzii, as for example in T2D, GDM, obesity, gout, pouchitis, chronic kidney disease, psoriasis, frailty, IBD, IBS, abdominal pain associated with IBS, and constipation diseases. The reduction, prevention or alleviation of a disorder or symptoms thereof can be measured by any appropriate assay. Preferably the reduction or alleviation of a disorder or symptoms is clinically and/or statistically significant, preferably with a probability value of <0.05. Such reduction, prevention, or alleviation of a disorder or symptoms are generally determined compared to an appropriate control subject or population, for example a healthy subject or an untreated or placebo treated subject, or the baseline level in an individual subject before treatment.

An appropriate mode of administration and formulation of the therapeutic agent is chosen depending on the treatment. A preferred mode of administration for probiotic bacteria or other supplements is oral or rectal.

Symbiotic combinations, or indeed any combinations of probiotic bacteria as described herein, can be prepared in oil based liquids (for example: medium chain triglycerides) using lyophilized material.

The preferred viability of the each strain in raw material ranges from $10^6$ CFU/g to $10^{10}$ CFU/g.

Administration into the subjects can be achieved via any of the delivery mode including enteric capsules, delayed or controlled release capsules, soft-gel capsules (e.g. chewable capsules), enteric coated capsules or capsules within capsules.

Administration can be achieved via ALU-ALU based sachet form of dosage with desiccant coatings.

Appropriate doses of the therapeutic agents as defined herein can be chosen by standard methods depending on the particular agent, the age, weight and condition of the patient, the mode of administration and the formulation concerned.

The therapeutic and prevention methods of the invention as described herein can be carried out on any type of subject or mammal which is capable of suffering from dysbiosis, e.g. gastrointestinal microbiota dysbiosis, especially in T2D, GDM obesity, gout, pouchitis, chronic kidney disease, psoriasis, frailty, IBD, IBS, abdominal pain associated with IBS and constipation diseases. The methods are generally carried out on humans.

The following are some examples of the invention, which are not meant to be limiting of the use of the invention herein but to show practical examples in detail of how the invention may be used.

Example 1

Isolation of Faecalibacterium prausnitzii and Desulfovibrio piger as Co-Culture

Surprisingly, Faecalibacterium prausnitzii FBT-22 (DSM 32186) and Desulfovibrio piger strain FBT-23 (DSM 32187) were isolated from the feces of healthy volunteer by microbiological pure culture technique under strict anaerobic condition (5% $H_2$, 15% $CO_2$ and 80% $N_2$) employed in a Coy chamber. The Postgate medium (PGM) was employed as routine culture medium for isolation and cultivation. The PGM contains (g/L); dipotassium phosphate: 0.5 g; ammonium chloride: 1; sodium lactate: 3.5; yeast extract: 1; Ascorbate: 0.1; cysteine: 0.5; sodium chloride: 1; peptone: 10; sodium sulphate: 1; calcium chloride dehydrate: 1; magnesium sulphate: 2; ferrous sulphate heptahydrate: 0.5. Sodium sulphate, magnesium sulphate heptahydrate, calcium chloride dehydrate were autoclaved separately while ferrous sulfateheptahydrate was filter sterilized 0.22 µm filter and added after autoclaving and mixing of all components. The final pH of the medium was adjusted with 1N NaOH or 1N HCl to 7.2±0.2.

The media was autoclaved at 100 kPa at 121° C. for 15 mins.

This medium lacks glucose which is the primary requirement for growth of F. prausnitzii however, contains relatively high amounts of lactate. The repeated subculturing leads to isolation of D. piger and F. prausnitzii.

Example 2

Alternative Isolation of a Strain of F. prausnitzii

A F. prausnitzii strain is isolated from the feces of a healthy volunteer by microbiological pure culture technique under strict anaerobic condition (5% $H_2$, 15% $CO_2$ and 80% $N_2$) employed in a Coy chamber. The routine culture medium for isolation contains following (g/L); yeast extract: 2.5; casitone: 10; glucose: 4.5; sodium chloride: 0.9; dipotasium phosphate: 0.45; potassium dihydrogen phosphate: 0.45; ammonium sulfate: 1.32; sodium bicarbonate: 4 g; cysteine: 1; resazurin: 0.001; hemin: 0.01. Vitamin mix contains: 10 µg biotin, 10 µg cobalamin, 30 µg p-aminobenzoic acid, 50 µg folic acid and 150 µg pyridoxamine. Final concentrations of short-chain fatty acids (SCFA) in the medium are 33 mM acetate, 9 mM propionate and 1 mM each of isobutyrate, isovalerate and valerate. All components are added aseptically while the tubes are flushed with $CO_2$. Heat labile vitamins are filter sterilized with 0.22 µm filter and added after the medium is autoclaved to give a final concentration of 0.05 µg thiamine $ml^{-1}$ and 0.05 µg riboflavin $ml^{-1}$. The final pH of the medium is adjusted with 1N NaOH or 1N HCl to 7.2±0.2. The media is autoclaved at 100 kPa at 121° C. for 15 mins.

Example 3

Alternative Isolation of a Strain of Desulfovibrio piger

A Desulfovibrio piger strain is isolated from the feces of healthy volunteer by microbiological pure culture technique under strict anaerobic condition (5% $H_2$, 15% $CO_2$ and 80% $N_2$) employed in a Coy chamber. The Postgate medium (PGM) is employed as routine culture medium for isolation and cultivation.

The postgate medium contains following (g/L); dipotassium phosphate: 0.5 g; ammonium chloride: 1; sodium lactate: 3.5; yeast extract: 1; Ascorbate: 0.1; cysteine: 0.5; sodium chloride: 1; peptone: 10; sodium sulphate: 1; calcium chloride dehydrate: 1; magnesium sulphate: 2; ferrous sulphate heptahydrate: 0.5. Sodium sulphate, magnesium sulphate heptahydrate, calcium chloride dehydrate are autoclaved separately while ferrous sulfate heptahydrate is filter sterilized 0.22 µm filter and added after autoclaving and mixing of all components. The final pH of the medium is adjusted with 1N NaOH or 1N HCl to 7.2±0.2.

The media is autoclaved at 100 kPa at 121° C. for 15 mins.

Example 4

Genomic Sequencing of *Faecalibacterium prausnitzii* DSM 32186

The aim of this study was to sequence the genome of the probiotic candidate *Faecalibacterium prausnitzii* DSM 32186 to identify factors important for metabolic interactions between *Faecalibacterium prausnitzii* DSM 32186 and *Desulfovibrio piger* DSM 32187.

Experimental Procedure and Results

Sequencing and Assembly

A culture of the strain *F. prausnitzii* DSM 32186 was harvested and DNA was isolated. The isolated DNA was sequenced on a Pacific Biosciences RS instrument, at SciLifeLab Uppsala, Sweden. Sequencing generated 73,071 reads with an N50 read length of 17,241 base pairs (bp). Sequence reads were assembled using the PacBio SMRT-Portal and HGAP version 3 assembly protocol (Chin et al., 2013). Default parameters were used except for setting the estimated genome size to 3 Mbp. Assembly resulted in a single contig of 2,915,013 bp with a mean coverage of 197. The assembly was circularized, duplicated trailing ends were trimmed with the AMOS package (Treangen et al., 2002) and the start of the chromosome was set to the DnaA gene start codon. To refine the assembly and circularization merged ends, the generated circularized chromosome was used as a reference in the SMRTPortal Resequence version 1 protocol that mapped the PacBio reads back to this reference and generates a consensus sequence. This consensus sequence was used for further analyses. Initial gene calling and annotation by the NCBI Prokaryotic Genome Annotation Pipeline (Angiuoli et al., 2008) indicated that the assembly contained an unnaturally high number of frameshifted genes (489 out of a total of 2,767 genes). Manual inspection of the assembly indicated that the frameshift occurred in homopolymer stretches of Gs or Cs with a length of about 6 bp. To mitigate the homopolymer problem, the same DNA sample was sent for sequencing using the Illumina technology at GATCBiotech.

A total of 7,624,279 paired end reads with a read length of 126 bp was generated with the Illumina Hiseq instrument. Trimmomatic 0.36 (Bolger et al., 2014) was used for read quality control and filtering of adapter sequences. A total of 6,424,651 high-quality paired-end reads were used in downstream analysis. The high quality reads were aligned to the PacBio generated consensus sequence with bowtie2 2.2.9 (Langmead and Salzberg, 2012) using default parameters except allowing insert size length of 600 bp (-X 600). Out of the high quality read pairs 90.2% aligned to the genome concordantly and the overall alignment rate was 99.75%. The alignment was supplied to Pilon (Walker et al., 2014) 1.18 (https://github.com/broadinstitute/pilon/releases) for correction of the assembly. Pilon made 1074 corrections to the assembly, the vast majority being single insertions of either G or C.

The final assembly of the *Faecalibacterium prausnitzii* DSM 32186 genome contained 2,905,188 base pairs and was submitted to NCBI and received the accession number CP015751.

Genome Annotation

The genome sequence was annotated with the NCBI Prokaryotic Genome Annotation Pipeline and a total of 2,737 genes were found on the chromosome out of which 2,608 were protein coding genes, 86 RNA genes and 43 pseudogenes. The genome contains 6 complete 5S, 16S and 23S ribosomal genes and 64 tRNA genes.

Unique Genetic Potential Compared to Other Sequenced *F. prausnitzii* Genomes The genome of *F. prausnitzii* DSM 32186 was annotated by the Rapid Annotation using Subsystem Technology (RAST) Server (http://rast.nmpdr.org/). A comparison of the annotation of genes in the sequenced genomes, *F. prausnitzii* A2-165, SL3/3, KLE1255, L2-6 and M212 to *F. prausnitzii* DSM 32186 identified the following unique functions are listed in Table 1.

Of special interest is the L-lactate dehydrogenase which is not found in any of the other sequenced *F prausnitzii* strains. This protein, A8C61_00370, in DSM 32186 do not have a close homolog in the other sequenced *F. prausnitzii* genomes and a sequence alignment search with BLAST to the NCBI nr database identifies L-lactate dehydrogenases from *Eubacterium, Oribacterium* and *Roseburia* as closely related sequences. The A8C61_00370 L-lactate dehydrogenase has likely been transferred into *F prausnitzii* DSM 32186 by horizontal gene transfer since it is in direct proximity to a genomic island identified by IslandViewer 3 (Dhillon et al., 2015) online tool (http://www.pathogenomics.sfu.ca/islandviewer/). Experimental data shows that the DSM 32186 strain produces more lactate during growth which is a substrate for *D piger* and therefore supports their interaction.

TABLE 1

Unique gene annotations in *F prausnitzii* DSM 32186 compared to the following sequenced *F. prausntizii* genomes. Bold strain names specifies the strain to which DSM 32186 has unique functions.

| M212:SL3/3 |
|---|
| Sucrose phosphorylase (EC 2.4.1.7) |
| L-alanine-DL-glutamate epimerase |
| tRNA (5-methylaminomethyl-2-thiouridylate)-methyltransferase (EC 2.1.1.61) |
| Beta-lactamase (EC 3.5.2.6) |
| A2-165:L2-6 |
| Serine hydroxymethyltransferase (EC 2.1.2.1) |
| CRISPR-associated helicase Cas3 |
| CRISPR-associated protein, Cas5e family |
| CRISPR-associated protein, Cse1 family |
| CRISPR-associated protein, Cse2 family |
| CRISPR-associated protein, Cse3 family |
| CRISPR-associated protein, Cse4 family |
| Ribonucleotide reductase of class Ia (aerobic), alpha subunit (EC 1.17.4.1) |

TABLE 1-continued

Unique gene annotations in *F. prausnitzii* DSM 32186 compared to the following sequenced *F. prausntizii* genomes. Bold strain names specifies the strain to which DSM 32186 has unique functions.

Ribonucleotide reductase of class Ia (aerobic), beta subunit (EC 1.17.4.1)
DNA primase/helicase, phage-associated
Autolysis response regulater LytR
Choline binding protein A
A2-165:M212

Putative predicted metal-dependent hydrolase
Transcriptional regulator, MerR family
A2-165:SL3/3

UDP-N-acetylglucosamine 2-epimerase (EC 5.1.3.14)
KLE1255:L2-6

L-asparaginase I, cytoplasmic (EC 3.5.1.1)
Alpha-galactosidase (EC 3.2.1.22)
PTS system, maltose and glucose-specific IIB component (EC 2.7.1.69)
PTS system, maltose and glucose-specific IIC component (EC 2.7.1.69)
Acetaldehyde dehydrogenase (EC 1.2.1.10)
tRNA S(4)U 4-thiouridine synthase (former ThiI)
KLE1255:M212 capsular polysaccharide biosynthesis protein
Multidrug and toxin extrusion (MATE) family efflux pump YdhE/NorM, homolog
KLE1255:SL3/3

Adenine-specific methyltransferase (EC 2.1.1.72)
Type III restriction-modification system methylation subunit (EC 2.1.1.72)
RNA polymerase sigma-54 factor RpoN
A2-165:KLE1255 putative esterase
Manganese-dependent protein-tyrosine phosphatase (EC 3.1.3.48)
Hydrolase (HAD superfamily) in cluster with DUF1447
Putative DNA-binding protein in cluster with Type I restriction-modification system
RelE/StbE replicon stabilization toxin
L2-6:M212:SL3/3

Phosphoglycerate mutase family
A2-165:M212:SL3/3

Galactose permease
Anion permease ArsB/NhaD-like
KLE1255:L2-6:M212

Potassium efflux system KefA protein
KLE1255:L2-6:SL3/3

Galactoside O-acetyltransferase (EC 2.3.1.18)
Anti-sigma B factor antagonist RsbV
KLE1255:M212:SL3/3

Chorismate mutase I (EC 5.4.99.5)
N-Acetyl-D-glucosamine ABC transport system, permease protein 1
Pectin degradation protein KdgF
Glycerol-3-phosphate ABC transporter, periplasmic glycerol-3-phosphate-binding protein (TC 3.A.1.1.3)
Inner membrane protein translocase component YidC, long form
Thermostable carboxypeptidase 1 (EC 3.4.17.19)
VapB protein (antitoxin to VapC)
A2-165:KLE1255:L2-6

Bipolar DNA helicase HerA
Ribosome-associated heat shock protein implicated in the recycling of the 50S subunit (S4 paralog)
Ubiquinone/menaquinone biosynthesis methyltransferase UbiE (EC 2.1.1.—)
tRNA-specific 2-thiouridylase MnmA
A2-165:KLE1255:M212

Phage tail fiber protein
A2-165:L2-6:M212:SL3/3

Phage major tail protein

TABLE 1-continued

Unique gene annotations in *F. prausnitzii* DSM 32186 compared to the following sequenced *F. prausntizii* genomes. Bold strain names specifies the strain to which DSM 32186 has unique functions.

NADH dehydrogenase (EC 1.6.99.3)
KLE1255:L2-6:M212:SL3/3

Cellobiose phosphotransferase system YdjC-like protein
Lactose and galactose permease, GPH translocator family
Pseudouridine-5' phosphatase (EC 3.1.3.—)
Duplicated ATPase component MtsB of energizing module of methionine-regulated ECF transporter
Substrate-specific component MtsA of methionine-regulated ECF transporter
Transmembrane component MtsC of energizing module of methionine-regulated ECF transporter
Phage major capsid protein
Aminopeptidase C (EC 3.4.22.40)
Rrf2 family transcriptional regulator, group III
YoeB toxin protein
A2-165:KLE1255:M212:SL3/3

Oligo-1,6-glucosidase (EC 3.2.1.10)
Co-activator of prophage gene expression IbrB
TTE0858 replicon stabilization protein (antitoxin to TTE0859)
A2-165:KLE1255:L2-6:M212:SL3/3

Maltodextrin glucosidase (EC 3.2.1.20)
Maltose O-acetyltransferase (EC 2.3.1.79)
L-lactate dehydrogenase (EC 1.1.1.27)
Maltose/maltodextrin ABC transporter, substrate binding periplasmic protein MalE
Choline kinase (EC 2.7.1.32)
Choline permease LicB
Cholinephosphate cytidylyltransferase (EC 2.7.7.15)
Lipopolysaccharide cholinephosphotransferase LicD1 (EC 2.7.8.—)
Alpha-L-Rha alpha-1,3-L-rhamnosyltransferase (EC 2.4.1.—)
Single-stranded exonuclease associated with Rad50/Mre11 complex
DNA mismatch repair endonuclease MutH
Very-short-patch mismatch repair endonuclease (G-T specific)
Mg(2+) transport ATPase protein C
Co-activator of prophage gene expression IbrA
Phage terminase small subunit
Phage replication initiation protein
tRNA-Ala
tRNA-Arg
tRNA-Asn
tRNA-Asp
tRNA-Cys
tRNA-Gln
tRNA-Glu
tRNA-Gly
tRNA-His
tRNA-Ile
tRNA-Leu
tRNA-Lys
tRNA-Met
tRNA-Phe
tRNA-Pro
tRNA-Ser
tRNA-Thr
tRNA-Trp
tRNA-Tyr
tRNA-Val
Cytochrome c-type biogenesis protein DsbD, protein-disulfide reductase (EC 1.8.1.8)
Glycine betaine transporter OpuD
HtrA protease/chaperone protein
Beta-lactamase class C and other penicillin binding proteins
L2-6

Phosphoribosylformimino-5-aminoimidazole carboxamide ribotide isomerase (EC 5.3.1.16)
ATP phosphoribosyltransferase (EC 2.4.2.17)
ATP phosphoribosyltransferase regulatory subunit (EC 2.4.2.17)
Histidinol dehydrogenase (EC 1.1.1.23)
Histidinol-phosphate aminotransferase (EC 2.6.1.9)
Imidazole glycerol phosphate synthase amidotransferase subunit (EC 2.4.2.—)
Imidazole glycerol phosphate synthase cyclase subunit (EC 4.1.3.—)
Imidazoleglycerol-phosphate dehydratase (EC 4.2.1.19)
Cellobiose phosphorylase (EC 2.4.1.—)
Citrate synthase (si) (EC 2.3.3.1)
N-acetylmuramoyl-L-alanine amidase (EC 3.5.1.28)

TABLE 1-continued

Unique gene annotations in *F. prausnitzii* DSM 32186 compared to the following sequenced *F. prausntizii* genomes. Bold strain names specifies the strain to which DSM 32186 has unique functions.

NAD(P)HX epimerase
Alcohol dehydrogenase (EC 1.1.1.1)
Isocitrate dehydrogenase [NADP] (EC 1.1.1.42)
Recombination inhibitory protein MutS2
Phosphate:acyl-ACP acyltransferase PlsX
Repressor CsoR of the copZA operon
TRAP-type C4-dicarboxylate transport system, small permease component
M212

Putative tRNA-m1A22 methylase
Phage portal protein
SL3/3

DinG family ATP-dependent helicase CPE1197
Alpha-aspartyl dipeptidase Peptidase E (EC 3.4.13.21)
A2-165

Beta-glucosidase (EC 3.2.1.21)
Beta-glucoside bgl operon antiterminator, BglG family
Maltose/maltodextrin ABC transporter, permease protein MalF
Maltose/maltodextrin ABC transporter, permease protein MalG
Glycerol kinase (EC 2.7.1.30)
Tyrosine-protein kinase EpsD (EC 2.7.10.2)
Tyrosine-protein kinase transmembrane modulator EpsC
Alpha-D-GlcNAc alpha-1,2-L-rhamnosyltransferase (EC 2.4.1.—)
TRAP-type transport system, small permease component, predicted N-acetylneuraminate transporter
Rod shape-determining protein RodA
RNA-binding protein Jag
3,4-dihydroxy-2-butanone 4-phosphate synthase (EC 4.1.99.12)
5-amino-6-(5-phosphoribosylamino)uracil reductase (EC 1.1.1.193)
6,7-dimethyl-8-ribityllumazine synthase (EC 2.5.1.78)
Diaminohydroxyphosphoribosylaminopyrimidine deaminase (EC 3.5.4.26)
GTP cyclohydrolase II (EC 3.5.4.25)
Riboflavin synthase eubacterial/eukaryotic (EC 2.5.1.9)
Chromosome partition protein smc
(2E,6E)-farnesyl diphosphate synthase (EC 2.5.1.10)
Dimethylallyltransferase (EC 2.5.1.1)
Octaprenyl diphosphate synthase (EC 2.5.1.90)
Lipid carrier: UDP-N-acetylgalactosaminyltransferase (EC 2.4.1.—)
Ferroxidase (EC 1.16.3.1)
Iron-binding ferritin-like antioxidant protein
Non-specific DNA-binding protein Dps
Superoxide reductase (EC 1.15.1.2)
transcriptional regulator, Crp/Fnr family
KLE1255

Undecaprenyl-phosphate galactosephosphotransferase (EC 2.7.8.6)
YafQ toxin protein
Formate dehydrogenase chain D (EC 1.2.1.2)

Example 5

Evaluation of the Synergistic Effects

To evaluate the synergistic effects a co-culture from Example 1 was used. As an alternative the *F. prausnitzii* strain FBT-22 (DSM 32186) from Example 2 was co-cultured with the *D. piger* strain FBT-23 (DSM 32187) from Example 3 in postgate medium under strict anaerobic conditions.

The postgate medium contains following (g/L); dipotassium phosphate: 0.5 g; ammonium chloride: 1; sodium lactate: 3.5; yeast extract: 1; Ascorbate: 0.1; cysteine: 0.5; sodium chloride: 1; peptone: 10; sodium sulphate: 1; calcium chloride dehydrate: 1; magnesium sulphate: 2; ferrous sulphate heptahydrate: 0.5. Sodium sulphate, magnesium sulphate heptahydrate, calcium chloride dehydrate were autoclaved separately while ferrous sulfate heptahydrate was filter sterilized 0.22 μm filter and added after autoclaving and mixing of all components. The final pH of the medium was adjusted with 1N NaOH or 1N HCl to 7.2±0.2.

The media was autoclaved at 100 kPa at 121° C. for 15 mins.

This resulted in the following data (Table 2), illustrating the synergistic effects of the strains on butyrate production.

TABLE 2

| | Fold change in fatty acid profile | | | |
|---|---|---|---|---|
| | Formate | Acetate | Butyrate | Lactate |
| Blank PGM | 1 | 1 | 1 | 1 |
| D. piger (D. p) FBT-23 | 0.8 | 118.5 | 1.1 | 0 |
| F. prausnitzii (F. p) FBT-22 | 0.9 | 1.4 | 7.1 | 1.1 |
| F. p FBT-22 + D. p FBT-23 | 0.8 | 122.7 | 25.2 | 0 |

Example 6

Manufacture of Product Containing Both Strains

In the present study we separately grew the *F. prausnitzii* strain FBT-22 (DSM 32186) and the *D. piger* strain FBT-23 (DSM 32187) in PGM under strict anaerobic conditions.

The PGM contains (g/L); dipotassium phosphate: 0.5 g; ammonium chloride: 1; sodium lactate: 3.5; yeast extract: 1; Ascorbate: 0.1; cysteine: 0.5; sodium chloride: 1; peptone: 10; sodium sulphate: 1; calcium chloride dehydrate: 1; magnesium sulphate: 2; ferrous sulphate heptahydrate: 0.5. Sodium sulphate, magnesium sulphate heptahydrate, calcium chloride dehydrate were autoclaved separately while ferrous sulfate heptahydrate was filter sterilized 0.22 μm filter and added after autoclaving and mixing of all components. The final pH of the medium was adjusted with 1N NaOH or 1N HCl to 7.2±0.2.

The media was autoclaved at 100 kPa at 121° C. for 15 mins.

After growing the bacteria into stationary phase, the cells where washed in distilled water and then concentrated using a centrifuge for sensitive material. The resulting slurry of each strain was measured in aliquots containing 1 E+9 CFU and then mixed with each other in ratio 1:1. The product was then preserved in 20% glycerol and kept at −80° C.

Example 7

Metabolic Profiles of Type Strain of *Faecalibacterium Prausnitzii* A2-165 (DSM 17677) and *Faecalibacterium prausnitzii* FBT-22 (DSM 32186) in Physiologically Relevant Medium LYBHI The detailed metabolic profiles of *Faecalibacterium prausnitzii* strains are depicted in FIG. 1 and FIG. 2. In aforementioned figures it is obvious that on glucose fermentation *F. prausnitzii* can produce butyrate as the major SCFA and consumes acetate. Additionally these bacteria produce lactate, formate and acetate.

Figure 3:
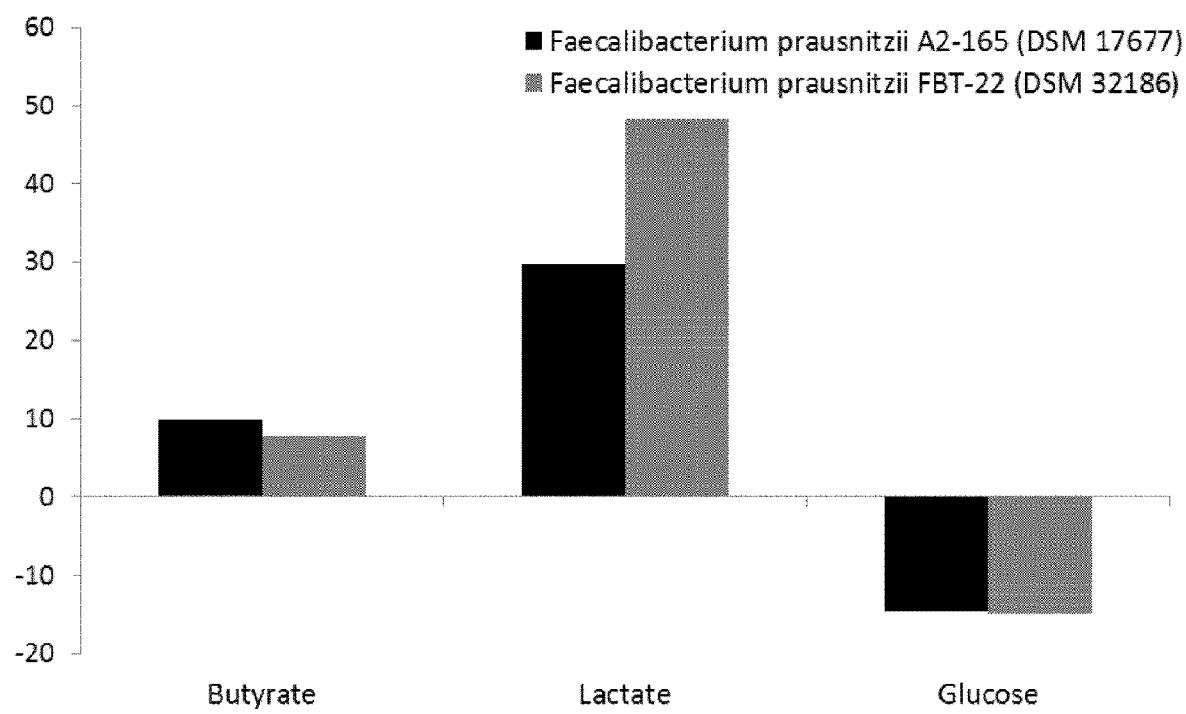
FIG. 3 shows the comparative SCFA profiles of *F. prausnitzii* isolate FBT-22 and type strain A2-165 in physiologically relevant growth medium, Brain Heart Infusion (LYBHI), y axis in mM.

The comparative metabolic profiles of type strain of *Faecalibacterium prausnitzii* A2-165 (DSM 17677) and *Faecalibacterium prausnitzii* FBT-22 (DSM 32186) in physiologically relevant medium LYBHI reveals that these two bacteria are metabolically different (Fold change of SCFA is shown in Table 3). The comparative glucose consumption and butyrate production was almost similar, however, the two strains differs in lactate production (FIG. 3)

Composition of physiologically relevant growth medium LYBHI:LYBHI medium (brain-heart infusion medium supplemented with 0.5% yeast extract) (Oxoid, UK) supplemented with 1 mg/ml cellobiose (Sigma-Aldrich Chemie GmbH, Buchs, Switzerland), 1 mg/ml maltose (Sigma-Aldrich), and 0.5 mg/ml cysteine (Sigma-Aldrich).

The complete carbon and electron balances are presented in Table 4.

Example 8

Metabolic Profiles of Mono-Culture and Co-Culture of Type Strain *Faecalibacterium prausnitzii* A2-165 (DSM 17677) and *Desulfovibrio piger* Strain FBT-23 (DSM 32187) in LYBHI Medium The synergistic effect of type strain *Faecalibacterium prausnitzii* A2-165 and *Desulfovibrio piger* strain FBT-23 was evaluated in LYBHI medium (composition described in Example 7).

As shown in FIG. 2, lactate produced by *F. prausnitzii* used as electron donor by *D. piger* and vice versa acetate generated by *D. piger* can be utilized by *F. prausnitzii* for butyrate production.

Figure 4:
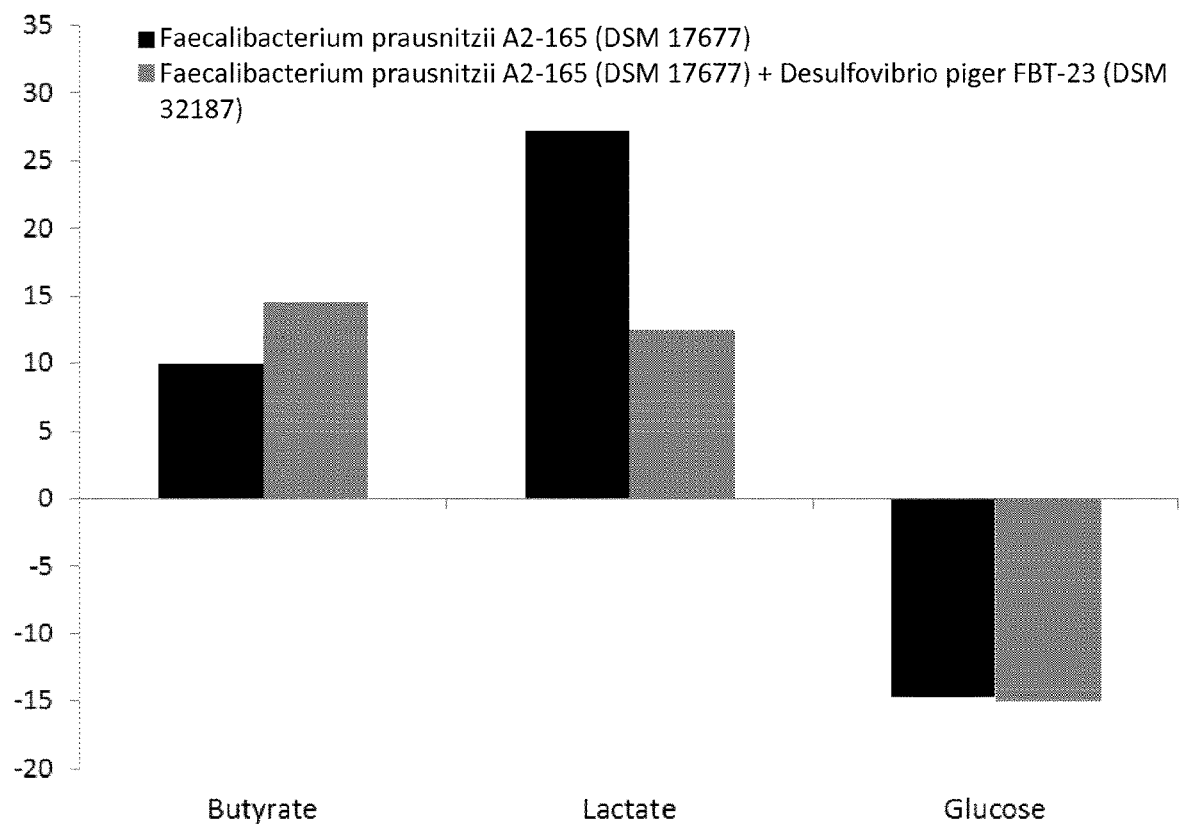
FIG. 4 shows the metabolic profiles of *F. prausnitzii* type strain A2-165 monoculture and coculture with *D. piger* in LYBHI growth medium, y axis in mM.

In LYBHI medium under the co-culture conditions butyrate production was 1.5 fold increased and lactate production was 2.3 fold decreased (FIG. 4, table 3). This indicates beneficial effect of co-culture/cross feeding i.e. increased butyrate production. The complete carbon and electron balances are presented in Table 4.

Example 9

Metabolic Profiles of Mono-Culture and Co-Culture of *Faecalibacterium prausnitzii* FBT-22 (DSM 32186) and *Desulfovibrio piger* Strain FBT-23 (DSM 32187) in LYBHI Medium The synergistic effect of *Faecalibacterium prausnitzii* FBT-22 and *Desulfovibrio piger* strain FBT-23 was evaluated in LYBHI medium (composition described in Example 7).

Figure 5:
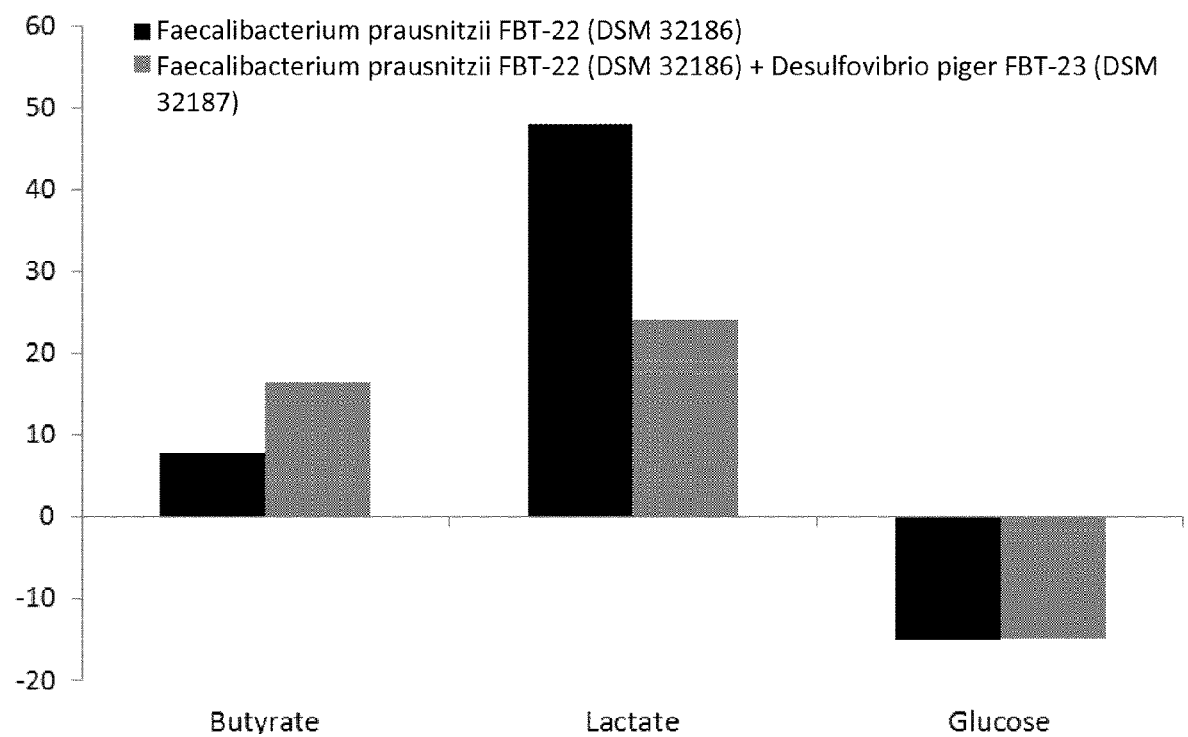
FIG. 5 shows the metabolic profiles of *F. prausnitzii* isolate FBT-22 monoculture and coculture with *D. piger* in LYBHI growth medium, y axis in mM.

In LYBHI medium, under co-culture conditions the butyrate production was 2.1 fold increased and lactate accumulation was 2 fold decreased (FIG. 5, Table 3). This shows that there is a cross feeding and synergistic effect.

The complete carbon and electron balances are presented in Table 4.

TABLE 3

Fold change SCFA of *Faecalibacterium prausnitzii* isolate and type strain A2-165 in physiologically relevant growth medium Brain Heart Infusion (LYBHI). The data illustrates the synergistic effects of the different strains on butyrate production.

|  | Butyrate | Acetate | Lactate |
| --- | --- | --- | --- |
| Blank LYBHI medium | 1.0 | 1.0 | 1.0 |
| *D. piger* FBT-23 (D. p) | 1.0 | 3.5 | 0.4 |
| *F. prausnitzii* FBT-22 (F. p) | 4.2 | 0.0 | 14.1 |
| F.p + D.p | 7.5 | 1.8 | 7.1 |
| *F. prausnitzii* type strain (F.p A2165) | 5.0 | 0.0 | 8.8 |
| F.p A2-165 + D.p | 6.8 | 0.0 | 3.8 |

TABLE 4 carbon and electron balance of mono-culture, co-cultures of *Faecalibacterium prausnitzii* FBT-22 (DSM 32186), *Faecalibacterium prausnitzii* A2-165 (DSM 17677) and *Desulfovibrio piger* strain FBT-23 (DSM 32187)

| Growth medium, bacterial strains and their respective combinations | | Butyrate | Lactate | Formate | Acetate | Glucose | % |
|---|---|---|---|---|---|---|---|
| Number of Carbon (C)/mol | | 4 | 3 | 1 | 2 | 6 | Recovery |
| Number of Electrons (e⁻)/mol | | 20 | 12 | 2 | 8 | 24 | |
| BHI medium | | | | | | | |
| *F. prausnitzii* A2-165 (DSM 17677) | mM | 9.9 | 29.8 | 0.0 | 0.0 | −14.6 | |
| | mM C | 40 | 89 | 0 | 0 | −88 | 141 |
| | mM e⁻ | 198 | 357 | 0 | 0 | −351 | 158 |
| *F. prausnitzii* A2-165 (DSM 17677) + *D. piger* FBT-23 (DSM 32187) | mM | 14.6 | 12.6 | 3.2 | 0.0 | −15.0 | |
| | mM C | 58 | 38 | 3 | 0 | −90 | 110 |
| | mM e⁻ | 292 | 151 | 6 | 0 | −360 | 125 |
| *F. prausnitzii* FBT-22 (DSM 32186) | mM | 7.8 | 48.3 | 0.0 | 0.0 | −15.0 | |
| | mM C | 31 | 145 | 0 | 0 | −90 | 196 |
| | mM e⁻ | 156 | 579 | 0 | 0 | −360 | 204 |
| *F. prausnitzii* FBT-22 (DSM 32186) + *D. piger* FBT-23 (DSM 32187) | mM | 16.5 | 24.1 | 0.0 | 0.0 | −15.0 | |
| | mM C | 66 | 72 | 0 | 2 | −90 | 151 |
| | mM e⁻ | 329 | 289 | 0 | 10 | −360 | 169 |

The invention claimed is:

1. A composition comprising (a) a *Faecalibacterium prausnitzii* strain and a strain of *Desulfovibrio piger* and (b) a preservative, a stabilizer, a gelling agent and/or a cryoprotectant,
   wherein the *D. piger* strain has one or more of the characteristics of: (i) producing acetate, (ii) consuming lactate and (iii) being an electron acceptor, and
   wherein the *F. prausnitzii* strain and the *D. piger* strain are the only bacterial strains present in the composition.

2. The composition of claim 1, wherein said *D. piger* strain has all of the characteristics (i) to (iii).

3. The composition of claim 1, wherein said strain of *F. prausnitzii* (i) produces butyrate, and optionally: (ii) consumes acetate, (iii) produces extracellular electrons and/or (iv) produces lactate, or any combination thereof.

4. The composition of claim 1, wherein said strain of *F. prausnitzii* has all of the characteristics (i) to (iv) and/or said strain of *D. piger* has all of the characteristics (i) to (iii).

5. The composition of claim 1, wherein said strain of *F. prausnitzii* comprises an L-lactate dehydrogenase gene.

6. The composition of claim 1, wherein the strain of *F. prausnitzii* and the strain of *D. piger* have a symbiotic relationship when in contact with each other results in increased growth of the *F. prausnitzii* strain and the *D. piger* strain and increased butyrate production by the *F. prausnitzii* strain.

7. The composition of claim 1, wherein the strain of *F. prausnitzii* is DSM 32186 and/or the strain of *D. piger* is DSM 32187.

8. The composition of claim 1, wherein the composition is lyophilized and/or dried.

9. The composition of claim 1, wherein the composition is in a unit dosage form of a capsule, a tablet or a gel.

10. The composition of claim 9, wherein the unit dosage form of the composition comprises about $10^4$ to $10^{12}$ colony forming units (cfu) of each of the *F. prausnitzii* strain and the *D. piger* strain.

11. A kit comprising:
   (i) a strain of *Faecalibacterium prausnitzii*;
   (ii) a strain of *Desulfovibrio piger*, wherein the *D. piger* strain has one or more of the characteristics of: (i) producing acetate, (ii) consuming lactate and (iii) being an electron acceptor; and
   (iii) a preservative, a stabilizer, a gelling agent and/or a cryoprotectant,
   wherein *F. prausnitzii* strain and the *D. piger* strain are the only bacterial strains present in the kit.

12. The kit of claim 11, wherein said strain of *F. prausnitzii* (i) produces butyrate, and optionally: (ii) consumes acetate, (iii) produces extracellular electrons and/or (iv) produces lactate, or any combination thereof.

13. The kit of claim 12, wherein said strain of *F. prausnitzii* has all of the characteristics (i) to (iv) and/or said strain of *D. piger* has all of the characteristics (i) to (iii).

14. The kit of claim 13, wherein the strain of *F. prausnitzii* is DSM 32186 and/or the strain of *D. piger* is DSM 32187.

15. A composition comprising the *Faecalibacterium prausnitzii* strain DSM 32186 and one or more of a cryoprotectant, a preservative, a stabilizer, and/or a gelling agent.

16. A composition comprising the *Desulfovibrio piger* strain DSM 32187 and one or more of a cryoprotectant, a preservative, a stabilizer, and/or a gelling agent.

17. A frozen, lyophilized or dried *Faecalibacterium prausnitzii* strain DSM 32186.

18. A frozen, lyophilized or dried *Desulfovibrio piger* strain DSM 32187.

* * * * *

UNITED STATES PATENT AND TRADEMARK OFFICE
CERTIFICATE OF CORRECTION

| | | |
|---|---|---|
| PATENT NO. | : 12,318,412 B2 | Page 1 of 11 |
| APPLICATION NO. | : 17/577208 | |
| DATED | : June 3, 2025 | |
| INVENTOR(S) | : Khan et al. | |

It is certified that error appears in the above-identified patent and that said Letters Patent is hereby corrected as shown below:

On the Title Page

Column 2, Lines 5-6, Item (56) References Cited, OTHER PUBLICATIONS, Foditch et al. cite:
Please correct "DOI: 0.1371/journal.pone.0116465" to read --DOI:10.1371/journal.pone.0116465--

In the Specification

Column 7, Line 28: Please correct "50.05," to read --≤0.05,--

Column 14, Line 28: Please correct "$10^1$" to read --$10^4$--

Columns 17-24, Table 1: Please delete Table 1 and replace with the following:

Signed and Sealed this
Thirtieth Day of September, 2025

John A. Squires
*Director of the United States Patent and Trademark Office*

TABLE 1

Unique gene annotations in F prausnitzii DSM 32186 compared to the following sequenced F. prausntizii genomes. Bold strain names specifies the strain to which DSM 32186 has unique functions.

| M212:SL3/3 |
| --- |
| Sucrose phosphorylase (EC 2.4.1.7) |
| L-alanine-DL-glutamate epimerase |
| tRNA (5-methylaminomethyl-2-thiouridylate)-methyltransferase (EC 2.1.1.61) |
| Beta-lactamase (EC 3.5.2.6) |
| A2-165:L2-6 |
| Serine hydroxymethyltransferase (EC 2.1.2.1) |
| CRISPR-associated helicase Cas3 |
| CRISPR-associated protein, Cas5e family |
| CRISPR-associated protein, Cse1 family |
| CRISPR-associated protein, Cse2 family |
| CRISPR-associated protein, Cse3 family |
| CRISPR-associated protein, Cse4 family |
| Ribonucleotide reductase of class Ia (aerobic), alpha subunit (EC 1.17.4.1) |
| Ribonucleotide reductase of class Ia (aerobic), beta subunit (EC 1.17.4.1) |
| DNA primase/helicase, phage-associated |
| Autolysis response regulater LytR |
| Choline binding protein A |

A2-165:M212

Putative predicted metal-dependent hydrolase

Transcriptional regulator, MerR family

A2-165:SL3/3

UDP-N-acetylglucosamine 2-epimerase (EC 5.1.3.14)

KLE1255:L2-6

L-asparaginase I, cytoplasmic (EC 3.5.1.1)

Alpha-galactosidase (EC 3.2.1.22)

PTS system, maltose and glucose-specific IIB component (EC 2.7.1.69)

PTS system, maltose and glucose-specific IIC component (EC 2.7.1.69)

Acetaldehyde dehydrogenase (EC 1.2.1.10)

tRNA S(4)U 4-thiouridine synthase (former ThiI)

KLE1255:M212 capsular polysaccharide biosynthesis protein

Multidrug and toxin extrusion (MATE) family efflux pump YdhE/NorM, homolog

KLE1255:SL3/3

Adenine-specific methyltransferase (EC 2.1.1.72)

Type III restriction-modification system methylation subunit (EC 2.1.1.72)

RNA polymerase sigma-54 factor RpoN

A2-165:KLE1255

| |
|---|
| putative esterase |
| Manganese-dependent protein-tyrosine phosphatase (EC 3.1.3.48) |
| Hydrolase (HAD superfamily) in cluster with DUF1447 |
| Putative DNA-binding protein in cluster with Type I restriction-modification system |
| RelE/StbE replicon stabilization toxin |
| L2-6:M212:SL3/3 |
| Phosphoglycerate mutase family |
| A2-165:M212:SL3/3 |
| Galactose permease |
| Anion permease ArsB/NhaD-like |
| KLE1255:L2-6:M212 |
| Potassium efflux system KefA protein |
| KLE1255:L2-6:SL3/3 |
| Galactoside O-acetyltransferase (EC 2.3.1.18) |
| Anti-sigma B factor antagonist RsbV |
| KLE1255:M212:SL3/3 |
| Chorismate mutase I (EC 5.4.99.5) |
| N-Acetyl-D-glucosamine ABC transport system, permease protein 1 |
| Pectin degradation protein KdgF |
| Glycerol-3-phosphate ABC transporter, periplasmic glycerol-3-phosphate-binding protein (TC 3.A.1.1.3) |

| |
|---|
| Inner membrane protein translocase component YidC, long form |
| Thermostable carboxypeptidase 1 (EC 3.4.17.19) |
| VapB protein (antitoxin to VapC) |
| A2-165:KLE1255:L2-6 |
| Bipolar DNA helicase HerA |
| Ribosome-associated heat shock protein implicated in the recycling of the 50S subunit (S4 paralog) |
| Ubiquinone/menaquinone biosynthesis methyltransferase UbiE (EC 2.1.1.-) |
| tRNA-specific 2-thiouridylase MnmA |
| A2-165:KLE1255:M212 |
| Phage tail fiber protein |
| A2-165:L2-6:M212:SL3/3 |
| Phage major tail protein |
| NADH dehydrogenase (EC 1.6.99.3) |
| KLE1255:L2-6:M212:SL3/3 |
| Cellobiose phosphotransferase system YdjC-like protein |
| Lactose and galactose permease, GPH translocator family |
| Pseudouridine-5' phosphatase (EC 3.1.3.-) |
| Duplicated ATPase component MtsB of energizing module of methionine-regulated ECF transporter |
| Substrate-specific component MtsA of methionine-regulated ECF transporter |

| |
|---|
| Transmembrane component MtsC of energizing module of methionine-regulated ECF transporter |
| Phage major capsid protein |
| Aminopeptidase C (EC 3.4.22.40) |
| Rrf2 family transcriptional regulator, group III |
| YoeB toxin protein |
| A2-165:KLE1255:M212:SL3/3 |
| Oligo-1,6-glucosidase (EC 3.2.1.10) |
| Co-activator of prophage gene expression IbrB |
| TTE0858 replicon stabilization protein (antitoxin to TTE0859) |
| A2-165:KLE1255:L2-6:M212:SL3/3 |
| Maltodextrin glucosidase (EC 3.2.1.20) |
| Maltose O-acetyltransferase (EC 2.3.1.79) |
| L-lactate dehydrogenase (EC 1.1.1.27) |
| Maltose/maltodextrin ABC transporter, substrate binding periplasmic protein MalE |
| Choline kinase (EC 2.7.1.32) |
| Choline permease LicB |
| Cholinephosphate cytidylyltransferase (EC 2.7.7.15) |
| Lipopolysaccharide cholinephosphotransferase LicD1 (EC 2.7.8.-) |
| Alpha-L-Rha alpha-1,3-L-rhamnosyltransferase (EC 2.4.1.-) |
| Single-stranded exonuclease associated with Rad50/Mre11 complex |

| |
|---|
| DNA mismatch repair endonuclease MutH |
| Very-short-patch mismatch repair endonuclease (G-T specific) |
| Mg(2+) transport ATPase protein C |
| Co-activator of prophage gene expression IbrA |
| Phage terminase small subunit |
| Phage replication initiation protein |
| tRNA-Ala |
| tRNA-Arg |
| tRNA-Asn |
| tRNA-Asp |
| tRNA-Cys |
| tRNA-Gln |
| tRNA-Glu |
| tRNA-Gly |
| tRNA-His |
| tRNA-Ile |
| tRNA-Leu |
| tRNA-Lys |
| tRNA-Met |
| tRNA-Phe |

| |
|---|
| tRNA-Pro |
| tRNA-Ser |
| tRNA-Thr |
| tRNA-Trp |
| tRNA-Tyr |
| tRNA-Val |
| Cytochrome c-type biogenesis protein DsbD, protein-disulfide reductase (EC 1.8.1.8) |
| Glycine betaine transporter OpuD |
| HtrA protease/chaperone protein |
| Beta-lactamase class C and other penicillin binding proteins |
| L2-6 |
| Phosphoribosylformimino-5-aminoimidazole carboxamide ribotide isomerase (EC 5.3.1.16) |
| ATP phosphoribosyltransferase (EC 2.4.2.17) |
| ATP phosphoribosyltransferase regulatory subunit (EC 2.4.2.17) |
| Histidinol dehydrogenase (EC 1.1.1.23) |
| Histidinol-phosphate aminotransferase (EC 2.6.1.9) |
| Imidazole glycerol phosphate synthase amidotransferase subunit (EC 2.4.2.-) |
| Imidazole glycerol phosphate synthase cyclase subunit (EC 4.1.3.-) |
| Imidazoleglycerol-phosphate dehydratase (EC 4.2.1.19) |
| Cellobiose phosphorylase (EC 2.4.1.-) |

| |
|---|
| Citrate synthase (si) (EC 2.3.3.1) |
| N-acetylmuramoyl-L-alanine amidase (EC 3.5.1.28) |
| NAD(P)HX epimerase |
| Alcohol dehydrogenase (EC 1.1.1.1) |
| Isocitrate dehydrogenase [NADP] (EC 1.1.1.42) |
| Recombination inhibitory protein MutS2 |
| Phosphate:acyl-ACP acyltransferase PlsX |
| Repressor CsoR of the copZA operon |
| TRAP-type C4-dicarboxylate transport system, small permease component |
| M212 |
| Putative tRNA-m1A22 methylase |
| Phage portal protein |
| SL3/3 |
| DinG family ATP-dependent helicase CPE1197 |
| Alpha-aspartyl dipeptidase Peptidase E (EC 3.4.13.21) |
| A2-165 |
| Beta-glucosidase (EC 3.2.1.21) |
| Beta-glucoside bgl operon antiterminator, BglG family |
| Maltose/maltodextrin ABC transporter, permease protein MalF |
| Maltose/maltodextrin ABC transporter, permease protein MalG |

| |
|---|
| Glycerol kinase (EC 2.7.1.30) |
| Tyrosine-protein kinase EpsD (EC 2.7.10.2) |
| Tyrosine-protein kinase transmembrane modulator EpsC |
| Alpha-D-GlcNAc alpha-1,2-L-rhamnosyltransferase (EC 2.4.1.-) |
| TRAP-type transport system, small permease component, predicted N-acetylneuraminate transporter |
| Rod shape-determining protein RodA |
| RNA-binding protein Jag |
| 3,4-dihydroxy-2-butanone 4-phosphate synthase (EC 4.1.99.12) |
| 5-amino-6-(5-phosphoribosylamino)uracil reductase (EC 1.1.1.193) |
| 6,7-dimethyl-8-ribityllumazine synthase (EC 2.5.1.78) |
| Diaminohydroxyphosphoribosylaminopyrimidine deaminase (EC 3.5.4.26) |
| GTP cyclohydrolase II (EC 3.5.4.25) |
| Riboflavin synthase eubacterial/eukaryotic (EC 2.5.1.9) |
| Chromosome partition protein smc |
| (2E,6E)-farnesyl diphosphate synthase (EC 2.5.1.10) |
| Dimethylallyltransferase (EC 2.5.1.1) |
| Octaprenyl diphosphate synthase (EC 2.5.1.90) |
| Lipid carrier : UDP-N-acetylgalactosaminyltransferase (EC 2.4.1.-) |
| Ferroxidase (EC 1.16.3.1) |
| Iron-binding ferritin-like antioxidant protein |

| |
|---|
| Non-specific DNA-binding protein Dps |
| Superoxide reductase (EC 1.15.1.2) |
| transcriptional regulator, Crp/Fnr family |
| KLE1255 |
| Undecaprenyl-phosphate galactosephosphotransferase (EC 2.7.8.6) |
| YafQ toxin protein |
| Formate dehydrogenase chain D (EC 1.2.1.2) |